(12) United States Patent
Rosomoff

(10) Patent No.: US 11,514,092 B2
(45) Date of Patent: *Nov. 29, 2022

(54) COMPUTERIZED METHOD AND APPARATUS FOR AUTOMATED DISTRIBUTED INGEST AND PRESENTATION OF MULTI-DOMAIN METRICS

(71) Applicant: Express Scripts Strategic Development, Inc., St. Louis, MO (US)

(72) Inventor: Peter Andrew Rosomoff, Wildwood, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 328 days.

This patent is subject to a terminal disclaimer.

(21) Appl. No.: 16/928,118

(22) Filed: Jul. 14, 2020

(65) Prior Publication Data

US 2020/0342010 A1 Oct. 29, 2020

Related U.S. Application Data

(63) Continuation of application No. 15/947,064, filed on Apr. 6, 2018, now Pat. No. 10,713,287.

(51) Int. Cl.
*G06F 16/33* (2019.01)
*G16H 20/10* (2018.01)
*G06F 16/31* (2019.01)
*G06F 16/93* (2019.01)

(Continued)

(52) U.S. Cl.
CPC .............. *G06F 16/33* (2019.01); *G06F 16/31* (2019.01); *G06F 16/93* (2019.01); *G06F 16/955* (2019.01); *G06F 40/18* (2020.01); *G16H 20/10* (2018.01)

(58) Field of Classification Search
CPC ........ G06F 16/955; G06F 16/31; G06F 16/33; G06F 16/332; G06F 16/93; G06H 20/10; G06H 40/20
See application file for complete search history.

(56) References Cited

U.S. PATENT DOCUMENTS

2017/0308519 A1 10/2017 Peng
2018/0246899 A1* 8/2018 Natchu ................... G06F 16/93

OTHER PUBLICATIONS

Alation; https://alation.com/; 2012.
(Continued)

*Primary Examiner* — Etienne P Leroux
(74) *Attorney, Agent, or Firm* — Harness IP

(57) ABSTRACT

A computerized search method includes receiving first input designating a first location of a first analytic. The method includes, in response to a scheduling event, obtaining a first document from the first location, identifying a first predefined label within the first document, obtaining first and second data associated with the first predefined label, storing the first datum into a value index as a current value of the first analytic, and storing the second datum into a text index as a textual description of the first analytic. The method includes presenting a search interface and, in response to receiving a search query from a user: identifying a set of result analytics relevant to the search query based on the text index and presenting, for each of the result analytics, a textual description of the analytic from the text index and a most recent value of the analytic from the value index.

20 Claims, 8 Drawing Sheets

(51) Int. Cl.
   *G06F 16/955* (2019.01)
   *G06F 40/18* (2020.01)

(56) References Cited

OTHER PUBLICATIONS

Connect by Alteryx, https://www.alteryx.com/products/alteryx-platform/alteryx-connect, Aug. 3, 2017.

* cited by examiner

COMPUTERIZED METHOD AND APPARATUS FOR AUTOMATED DISTRIBUTED INGEST AND PRESENTATION OF MULTI-DOMAIN METRICS

CROSS-REFERENCE TO RELATED APPLICATIONS

This application is a continuation of U.S. patent application Ser. No. 15/947,064, filed on Apr. 6, 2018; the entire disclosure of which is incorporated herein by reference.

FIELD

The present disclosure relates to computerized search engines, and more particularly to natural language text-based computerized search engines.

BACKGROUND

Traditional search engines crawl a set of documents, such as web pages, and attempt to infer semantic meaning from contents and metadata of those documents. Traditional search engines, however, are not adept at identifying which portions of these documents are most important, especially when the documents are data-intensive. For example, while a traditional search engine may be able to index text found within cells of a spreadsheet, the search engine may not have any understanding of the meaning or importance of data within the spreadsheet.

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

A computerized search method includes specifying a first predefined label for use with the computerized search method. The method includes receiving first input designating a first location of a first analytic. The method includes, in response to a scheduling event, (i) obtaining a first document from the first location, (ii) identifying the first predefined label within the first document, (iii) obtaining a first datum associated with the first predefined label from the first document, (iv) storing the first datum into a value index as a current value of the first analytic, (v) obtaining a second datum associated with the first predefined label from the first document, and (vi) storing the second datum into a text index as a textual description of the first analytic. The method includes presenting a search interface. The method includes, in response to receiving a search query from a user via the search interface: identifying a set of result analytics relevant to the search query based on the text index and, using the search interface, presenting, for each analytic of the set of result analytics, a textual description of the analytic from the text index and a most recent value of the analytic from the value index.

In other features, the method includes receiving second input designating a second location of a second analytic and position data and storing the second location and the position data. The method includes, in response to a second scheduling event, obtaining a second document from the second location, extracting a value from within the second document at a position specified by the position data, and storing the value into the value index as a current value of the second analytic.

In other features, the method includes receiving second input designating a second location of a second analytic. The method includes, in response to a second scheduling event, obtaining a second document from the second location, extracting a set of values from a set of predefined positions within the second document, obtaining a third document from a third location, extracting a third datum from the third document at a position specified by the set of values, and storing the third datum into the value index as a current value of the second analytic.

In other features, the method includes extracting the third location from a predefined position within the second document. In other features, the method includes, in response to the second scheduling event, extracting a text value from a predefined position within the second document and storing the text value into the text index as a textual description of the second analytic.

In other features, the first document is a spreadsheet workbook. A worksheet of the workbook is selected in response to a name of the selected worksheet matching the first predefined label. The first datum is obtained from a first predetermined row and a first predetermined column of the selected worksheet. The second datum is obtained from the first predetermined row and a second predetermined column of the selected worksheet. In other features, the first location is a uniform resource locator (URL).

In other features, the method includes, in response to the scheduling event, determining whether a modification date is available for the first document. The method includes, in response to determining that the modification date is available for the first document, obtaining the modification date, comparing the modification date to a most recent acquisition date of the first analytic, and obtaining the first document only if the modification date is later than the most recent acquisition date.

In other features, the first document is a file located in a file store controlled by an operating system. The modification date is obtained by sending a request to the operating system. In other features, the method includes receiving second input specifying a refresh schedule of the first analytic, storing information specifying the refresh schedule associated with the first analytic, and generating the scheduling event based on the refresh schedule.

In other features, the method includes, in response to obtaining the first document from the first location, extracting a list associated with the first predefined label from the first document. The list identifies a set of analytics including the first analytic. The method includes, for each analytic of the set of analytics, storing an associated value into the value index as a current value of the analytic and storing an associated textual description into the text index as a textual description of the analytic.

In other features, the first document includes tabular data. Each of the set of analytics corresponds to a different row of the tabular data. Textual descriptions for the set of analytics are located in a first column of the tabular data. Values for the set of analytics are located in a second column of the tabular data. In other features, the method includes, in response to obtaining the first document, acquiring, from a predefined position in the first document with respect to the first predefined label, identification information for an author of the first analytic. The method includes selectively displaying the identification information to the user when the first analytic is included in the set of result analytics.

In other features, the method includes, in response to obtaining the first document, acquiring, from a second predefined position in the first document with respect to the first predefined label, contact information for the author and selectively displaying the contact information to the user when the first analytic is included in the set of result analytics. In other features, the method includes, in response to obtaining the first document, acquiring, from a predefined position in the first document with respect to the first predefined label, an access uniform resource locator (URL) for a source of data underlying the first analytic. The method includes selectively displaying the access URL to the user when the first analytic is included in the set of result analytics.

In other features, the method includes, in response to obtaining the first document, acquiring, from a predefined position in the first document with respect to the first predefined label, a modification timestamp for the first analytic and controlling generation of a future scheduling event based on the modification timestamp. In other features, the method includes, in response to obtaining the first document, acquiring, from a predefined position in the first document with respect to the first predefined label, a name of the first analytic. The method includes storing the name into the text index for the first analytic. In other features, the method includes operating a web server configured to receive the first input and present the search interface.

A system includes at least one processor and a computer-readable medium configured to store instructions for execution by the at least one processor. The instructions include specifying a first predefined label for use with the computerized search method. The instructions include receiving first input designating a first location of a first analytic. The instructions include, in response to a scheduling event: (i) obtaining a first document from the first location, (ii) identifying the first predefined label within the first document, (iii) obtaining a first datum associated with the first predefined label from the first document, (iv) storing the first datum into a value index as a current value of the first analytic, (v) obtaining a second datum associated with the first predefined label from the first document, and (vi) storing the second datum into a text index as a textual description of the first analytic. The instructions include presenting a search interface. The instructions include, in response to receiving a search query from a user via the search interface, identifying a set of result analytics relevant to the search query based on the text index and, using the search interface, presenting, for each analytic of the set of result analytics, a textual description of the analytic from the text index and a most recent value of the analytic from the value index.

A non-transitory computer-readable medium stores processor-executable instructions including specifying a first predefined label for use with the computerized search method. The instructions include receiving first input designating a first location of a first analytic. The instructions include, in response to a scheduling event: (i) obtaining a first document from the first location, (ii) identifying the first predefined label within the first document, (iii) obtaining a first datum associated with the first predefined label from the first document, (iv) storing the first datum into a value index as a current value of the first analytic, (v) obtaining a second datum associated with the first predefined label from the first document, and (vi) storing the second datum into a text index as a textual description of the first analytic. The instructions include presenting a search interface. The instructions include, in response to receiving a search query from a user via the search interface, identifying a set of result analytics relevant to the search query based on the text index and, using the search interface, presenting, for each analytic of the set of result analytics, a textual description of the analytic from the text index and a most recent value of the analytic from the value index.

Further areas of applicability of the present disclosure will become apparent from the detailed description, the claims, and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings.

In the drawings, reference numbers may be reused to identify similar and/or identical elements.

DETAILED DESCRIPTION

Introduction

Figure 1:
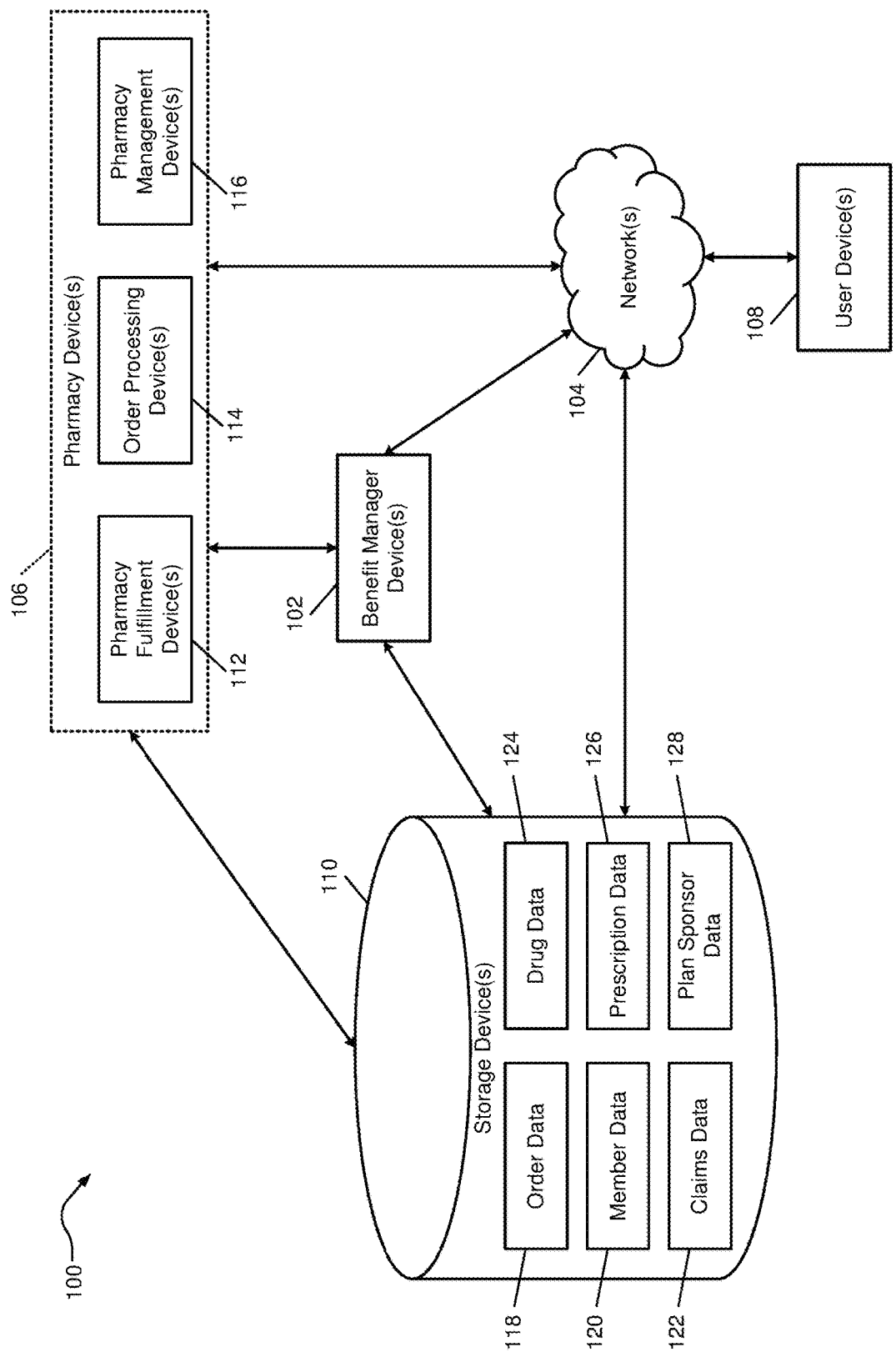
FIG. 1 is a functional block diagram of an example system including a high-volume pharmacy.

In data-rich environments, analysts prepare analyses for use by various end users by identifying and gathering data and generating metrics (also called analytics) based on the data. For example, engineers may refine manufacturing processes based on quality or timing metrics of a manufacturing system. Business managers may make investment decisions based on certain metrics. Users in sales and marketing may target their efforts based on metrics. Legal and compliance users may rely on metrics to certify statements to a regulator, licensor, etc. Certain metrics may be difficult to create, relying on data from a variety of sources and sophisticated classification and processing techniques. Further, these metrics may change over time. In many instances, these metrics may explicitly be time-based, such as a measure of manufacturing output in a prior week.

Even though an analyst may have prepared a first metric, other analysts (and especially non-analyst end users) may not be aware of the metric or recall that the first metric exists. The users may then request that an analyst recreate the first metric. In some environments, even the original analyst may have forgotten about the creation of the first metric. Traditionally, the output of analysts can be distributed to various end users via email distribution lists, which may announce the creation of new metrics and may periodically provide reports including the metrics. When a user needs a metric, the user would traditionally consult their own memory and then review their email system; then, users might need to discuss the availability of metrics among themselves and with analysts.

The present disclosure describes a technological solution to the inefficient and uncoordinated approach to analysis distribution and discovery. A publisher, who may be the analyst themselves, creates a computer-readable description of a metric that may be of interest and is not readily available elsewhere. This computer-readable description is prepared according to the principles of the present disclosure and specifies information about the metric, including a textual description of the metric, a source from which the metric can be obtained, and the schedule on which the metric is updated.

This computer-readable description is provided to a harvesting system that will, according to the specified schedule, obtain the most recent value for that metric and store that value in a search engine. The search engine is made accessible to users, who can then query the search engine to find answers to their questions. These answers take the form of the metrics obtained by the harvesting system.

For users who are aware that a certain metric exists, the search engine provides rapid retrieval and display of the answer without a manual process of consulting colleagues or analysts. In other words, because the search engine obtains and is configured to present the value of the metric, the value can be immediately displayed to the user, without the user having to navigate to the source of the analysis. Further, there is no delay caused by opening particular software (such as a spreadsheet program) or retrieving a file (such as a large spreadsheet) over a network connection. However, for additional metrics or background information, the search engine may offer a link for the user to easily reach the source of the analysis. In various situations, metrics may be displayed to users who don't even have installed software that is capable of accessing the underlying data source. For example, a business manager may be able to see a value for a metric even though the business manager does not have a database program capable of performing a SQL query.

Meanwhile, a user who is unaware of a metric can discover the existence of the metric through the search engine. In addition, the search engine may accumulate historical values of the metrics, creating an easily accessible historical record of metrics that may not even be available from the analysis source. In contrast to traditional search systems, the search engine of the present disclosure does not attempt to parse the text from the content and metadata of a document and infer semantic meaning. Instead, the harvesting system relies on the computer-readable description of the metric to describe and directly access the metric itself from the analysis source.

Although traditional search systems may be able to present excerpts from a document, such as excerpts including a specified text keyword, there is no guarantee in data-intensive analytical sources that any given metric will be within close proximity to descriptive text corresponding to the user's query, or that the proximate text will be adequately descriptive to anyone other than the originating analyst. Analysts may use complex data structures in spreadsheets, databases, and business intelligence (BI) software to aggregate, process, and condense data. As a result, the metric may correspond to a certain cell within a spreadsheet or a certain field within a certain record of a database. The publisher of the metric can indicate to the harvesting system this precise location, which a traditional search engine would never be able to identify.

The publisher may specify a textual description for the metric as well as a description of the units of the metric. In various implementations, each metric is a single value. In other implementations, a metric may be a set of values, such as a list of key-value pairs, which may be used to construct a pie chart, histogram, bar chart, etc.

The publisher may specify a wide variety of schedules based on day of the week, day of the month, or some other periodic or non-periodic schedule. In various implementations, the publisher can specify a triggering event that will indicate that a new value for the metric may be available. As described in more detail below, the harvesting system may implement a number of optimizations, such as only acquiring a new value of a metric if the source of the metric has changed since the metric was last acquired.

The search engine may index and reveal information about the analyst who produced the metric as well as the publisher who published the metric to the search engine. This may be used by users to assess the credibility or scope of the metric. Further, the analyst or publisher may associate a value with a metric indicating how authoritative the metric is. For example, when the metric is first created, the metric may have no indicia of authority. However, over time, users of the metric or data governance specialists may certify that the metric can be relied upon as authoritative. Such designation may be time-limited, lapsing after a predetermined time has passed and requiring reverification.

Special permissions may be assigned to the harvesting system so that the harvesting system can access metrics across a heterogeneous organization. The harvesting system may associate access rights with each metric and therefore provide the metric only to users having sufficient access. In various implementations, the search engine may be programmed to inform unauthorized users of the existence of a metric while obscuring the value of the metric itself. In this way, users can recognize that the metric exists and seek access if necessary for their job responsibilities. In traditional systems, users who do not have access to certain data may assume that the metric does not exist and seek to recreate it.

Business discussions and decisions frequently rely on understanding metrics obtained from data analysis. The explosion of data analysis even in small organizations has quickly surpassed the ability of individual people to locate and catalog the analysis. In some ways, this is analogous to the early days of the Web. However, the search engines developed for the Web are not well-positioned to obtain specific analytics of interest to users. The increasing speed of business decisions demands not only the ability to identify that an analytic exists, but to obtain the metrics as quickly as possible.

A search system according to the principles of the present disclosure may answer all of these needs, providing users with a natural language interface that returns metric information related to a query as well as context, links to source documents, author information, and an indication of freshness. Such a system may immediately expose a much greater set of data analysis to its users, with no limitation on its growth for future data analysis. This allows the users to speed and improve the decision-making and strategy development process by removing a number of impediments to obtaining quality metrics.

For example, in an organization that operates a high-volume pharmacy, a number of pharmacy-benefit-related metrics and pharmacy shipping metrics may be developed and will be of interest to a variety of users. For example, one metric may answer the question of how many scripts were shipped in the prior week. Another metric may answer the question of what percentage of members used a web interface for refill transactions in the prior month. Operation of such a high-volume pharmacy, including a number of components that produce data for analysis, is described in more detail below.

High-Volume Pharmacy

FIG. 1 is a block diagram of an example implementation of a system 100 for a high-volume pharmacy, according to an example implementation. While the system 100 is generally described as being deployed in a high-volume pharmacy or a fulfillment center (e.g., a mail order pharmacy, a direct delivery pharmacy, etc., and the like), the system 100 and/or components thereof may otherwise be deployed (e.g., in a lower volume pharmacy, etc.). A high-volume pharmacy may be a pharmacy that is capable of filling prescriptions automatically, mechanically, manually, or a combination thereof. The system 100 may include a benefit manager device 102, a pharmacy device 106, and one or more user devices 108 in communication with each other directly and/or over a network 104. The system may also include a storage device 110.

The benefit manager device 102 is a device operated by an entity that is at least partially responsible for creation and/or management of the pharmacy or drug benefit. While such entity operating the benefit manager device 102 is typically a pharmacy benefit manager (PBM), other entities may operate the benefit manager device 102 on behalf of themselves (i.e., the PBMs) or other entities. For example, the benefit manager device 102 may be operated by a health plan, a retail pharmacy chain, a drug wholesaler, a data analytics, or other type of software-related company, etc., or the like. In some implementations, a PBM that provides the pharmacy benefit may also provide one or more than one additional benefits including a medical or health benefit, a dental benefit, a vision benefit, a wellness benefit, a radiology benefit, a pet care benefit, an insurance benefit, a long term care benefit, a nursing home benefit, etc., and the like. The PBM may, in addition to its PBM operations, operate one or more than one pharmacies. The pharmacies may be retail pharmacies, mail order pharmacies, etc.

Some of the operations of the PBM that operates the benefit manager device 102 may include the following activities and processes. A member (or a person on behalf of the member) of a pharmacy benefit plan may obtain a prescription drug at a retail pharmacy location (e.g., a location of a physical store, etc.) from a pharmacist or a pharmacist technician. The member may also obtain the prescription drug through mail order drug delivery from a mail order pharmacy location, which may be the high-volume pharmacy system 100. In some implementations, the member may obtain the prescription drug directly or indirectly through the use of a machine, such as a kiosk, vending unit, mobile electronic device, or a different type of mechanical, electrical, electronic communication device and/or computing device. Such a machine may be filled with the prescription drug in prescription packaging, which may include multiple prescription components, by the high-volume pharmacy system 100. The pharmacy benefit plan is administered by or through the benefit manager device 102.

The member may have a copayment for the prescription drug that reflects an amount of money that the member is responsible to pay the pharmacy for the prescription drug. The money paid by the member to the pharmacy may come from personal funds of the member, a health savings account (HSA) of the member or the member's family, a health reimbursement arrangement (HRA) of the member or the member's family, a flexible spending account (FSA) of the member or the member's family, etc., or the like. In some instances, an employer of the member may directly or indirectly fund or reimburse the member for the copayments.

The amount of the copayment required by the member may vary with different pharmacy benefit plans having different plan sponsors or clients and/or for different prescription drugs. The member's copayment may be a flat copayment (e.g., $10, etc.), co-insurance (e.g., 10%, etc.), and/or a deductible (e.g., for first $500 of annual prescription drug expense, etc.) for certain prescription drugs, certain types and/or classes of prescription drugs, and/or all prescription drugs. The copayment may be stored in the storage device 110 or determined by the benefit manager device 102.

In some instances, the member may not pay the copayment or may only pay a portion of the copayment for the prescription drug. For example, if a usual and customary cost for a generic version of a prescription drug is $4, and the member's flat copayment is $20 for the prescription drug, the member may only need to pay $4 to receive the prescription drug. In another example involving a worker's compensation claim, no copayment may be due by the member for the prescription drug.

In addition, copayments may also vary based on different delivery channels used for the prescription drug to be received. For example, the copayment for receiving the prescription drug from a mail order pharmacy location may be less than the copayment for receiving the prescription drug from a retail pharmacy location.

In conjunction with receiving a copayment (if any) from the member and dispensing the prescription drug to the member, the pharmacy submits a claim to the PBM for the prescription drug. After receiving the claim, the PBM, e.g., the benefit manager device 102, may perform certain adjudication operations including verifying eligibility for the member, identifying/reviewing an applicable formulary for the member to determine any appropriate copayment, coinsurance, and deductible for the prescription drug, and performing a drug utilization review (DUR) on the member. Further, the PBM may provide a response to the pharmacy, e.g., the pharmacy system 100, following performance of at least some of the aforementioned operations.

As part of the adjudication, a plan sponsor (or the PBM on behalf of the plan sponsor) ultimately reimburses the pharmacy for filling the prescription drug when the prescription drug was successfully adjudicated.

The aforementioned adjudication operations generally occur before the copayment is received and the prescription drug is dispensed. However in some instances, these operations may occur simultaneously, substantially simultaneously, or in a different order. In addition, more or less adjudication operations may be performed as at least part of the adjudication process.

The amount of reimbursement paid to the pharmacy by a plan sponsor and/or money paid by the member may be determined at least partially based on types of pharmacy network in which the pharmacy is included. In some implementations, the amount may also be determined based on other factors. For example, if the member pays the pharmacy for the prescription drug without using the prescription or drug benefit provided by the PBM, the amount of money paid by the member may be higher than when the member uses the prescription or drug benefit. In some implementations, the amount of money received by the pharmacy for dispensing the prescription drug and for the prescription drug itself may be higher than when the member uses the prescription or drug benefit. Some or all of the foregoing operations may be performed by executing instructions stored in the benefit manager device 102 and/or an additional device.

Examples of the network 104 include Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. The network 104 may include an optical network. The network 104 may be a local area network or a global communication network, such as the Internet. In some implementations, the network 104 may include a network dedicated to prescription orders, e.g., a prescribing network such as the electronic prescribing network operated by Surescripts of Arlington, Va.

Moreover, although the system shows a single network 104, multiple networks can be used. The multiple networks may communicate in series with each other to link the devices 102-110 or in parallel to link the devices 102-110.

The pharmacy device 106 may be a device associated with a retail pharmacy location (e.g., an exclusive pharmacy location, a grocery store with a retail pharmacy, or a general sales store with a retail pharmacy) or other type of pharmacy location at which a member attempts to obtain a prescription. The pharmacy device 106 may be utilized by the pharmacy to submit the claim to the PBM for adjudication.

Additionally, in some implementations, the pharmacy device 106 may enable information exchange between the pharmacy and the PBM, for example, to allow the sharing of member information such as drug history, and the like, that may allow the pharmacy to better service a member (e.g., by providing more informed therapy consultation and drug interaction information, etc.). In some implementations, the benefit manager device 102 may track prescription drug fulfillment and/or other information for users that are not members or have not identified themselves as members, at the time (or in conjunction with the time) in which they seek to have a prescription filled at a pharmacy.

The pharmacy device 106 may include a pharmacy fulfillment device 112, an order processing device 114, and a pharmacy management device 116 in communication with each other directly and/or over the network 104.

The order processing device 114 may receive information regarding filling prescriptions and may direct an order component to one or more devices of the pharmacy fulfillment device 112 at a pharmacy. The pharmacy fulfillment device 112 may fulfill, dispense, aggregate, and/or pack the order components of the prescription drugs in accordance with one or more prescription orders directed by the order processing device 114. The order processing device 114 may be deployed in the system 100, or may otherwise be used.

In general, the order processing device 114 is a device located within or otherwise associated with the pharmacy to enable fulfillment of a prescription and dispensing prescription drugs by the pharmacy fulfillment device 112. In some implementations, the order processing device 114 may be an external order processing device separate from the pharmacy and communicate with other devices located within the pharmacy.

For example, the external order processing device may communicate with an internal pharmacy order processing device and/or other devices located within the system 100.

In some implementations, the external order processing device may have limited functionality (e.g., as operated by a user requesting fulfillment of a prescription drug), while the internal pharmacy order processing device may have greater functionality (e.g., as operated by a pharmacist).

The order processing device 114 may track the prescription order as it is fulfilled by the pharmacy fulfillment device 112. The prescription order may include one or more than one prescription drugs to be filled by the pharmacy. The order processing device 114 may make pharmacy routing decisions and/or order consolidation decisions for the particular prescription order. The pharmacy routing decisions include what device(s) in the pharmacy are responsible for filling or otherwise handling certain portions of the prescription order. The order consolidation decisions include whether portions of one prescription order or multiple prescription orders should be shipped together for a user or a user family. The order processing device 114 may also track and/or schedule literature or paperwork associated with each prescription order or multiple prescription orders that are being shipped together. In some implementations, the order processing device 114 may operate in combination with the pharmacy management device 116.

The order processing device 114 may include circuitry, a processor, a memory to store data and instructions, and communication functionality. The order processing device 114 is dedicated to performing processes, methods and/or instructions described herein. Other types of electronic devices specifically configured to implement with the processes, methods and/or instructions described herein may also be used.

In some implementations, at least some functionalities of the order processing device 114 may be included in the pharmacy management device 116. The order processing device 114 may be in a client-server relationship with the pharmacy management device 116, in a peer-to-peer relationship with the pharmacy management device 116, or in a different type of relationship with the pharmacy management device 116. The order processing device 114 and/or the pharmacy management device 116 may communicate directly (e.g., by utilizing a local storage, etc.) and/or through the network 104 (e.g., by utilizing a cloud configuration or software as a service. etc.) with the storage device 110.

The user device 108 is used by a device operator. The device operator may be a user (e.g., an employee, a contractor, a benefit member, etc.) associated with a software development project. Other device operators may also operate the user device 108. The user device 108 may be a stand-alone device that solely provides at least some of the functionality to enable analysis of software development risks, or may be a multi-use device that has functionality outside of analysis of software development risks. Examples of the user device 108 include a set-top box (STB), a receiver card, a mobile telephone, a personal digital assistant (PDA), a display device, a portable gaming unit, and a computing system, etc. Other devices, however, may also be used. In some embodiments, the computing system may include a mobile computing device. For example, the user device 108 may include a mobile electronic device, such an iPhone or iPad by Apple, Inc., mobile electronic devices powered by Android by Google, Inc., and a Blackberry by Research In Motion Limited. The user device 108 may also include other computing devices, such as desktop computing devices, notebook computing devices, netbook computing devices, gaming devices, and the like. Other types of electronic devices may also be used.

The storage device 110 may include: a non-transitory storage (e.g., memory, hard disk, CD-ROM, etc.) in communication with the benefit manager device 102, the pharmacy device 106, and/or the user device 108 directly and/or over the network 104. The non-transitory storage may store order data 118, member data 120, claims data 122, drug data 124, prescription data 126, and/or plan sponsor data 128. Further, the system 100 may include additional devices, which may communicate with each other directly or over the network 104.

The order data 118 may be related to a prescription order. The order data may include type of the prescription drug (e.g., drug name and strength, etc.) and quantity of the prescription drug, etc. The order data 118 may also include data used for completion of the prescription, such as prescription materials. In general, prescription materials include an electronic copy of information regarding the prescription drug for inclusion with or otherwise in conjunction with the fulfilled prescription. The prescription materials may include electronic information regarding drug interaction warnings, recommended usage, possible side effects, expiration date, date of prescribing, or the like. The order data 118 may be used by a high volume fulfillment center to fulfill a pharmacy order.

In some implementations, the order data 118 includes verification information associated with fulfillment of the prescription in the pharmacy. For example, the order data 118 may include videos and/or images taken of (i) the prescription drug prior to dispensing, during dispensing, and/or after dispensing, (ii) the prescription container (e.g., a prescription container and sealing lid, prescription packaging and the like) used to contain the prescription drug prior to dispensing, during dispensing, and/or after dispensing, (iii) the packaging and/or packaging materials used to ship or otherwise deliver the prescription drug prior to dispensing, during dispensing, and/or after dispensing, and/or (iv) the fulfillment process within the pharmacy. Other types of verification information such as bar code data read from pallets, bins, trays, carts, and the like used to transport prescriptions within the pharmacy may also be stored as order data 118.

The member data 120 includes information regarding the members associated with the PBM. The information stored as member data 120 may include personal information, personal health information, protected health information, and the like. Examples of the member data 120 include name, address, telephone number, e-mail address, prescription drug history, etc., and the like. The member data 120 may include a plan sponsor identifier that identifies the plan sponsor associated with the member and/or a member identifier that identifies the member to the plan sponsor. The member data 120 may include a member identifier that identifies the plan sponsor associated with the user and/or a user identifier that identifies the user to the plan sponsor. The member data 120 may also include, by way of example, dispensation preferences such as type of label, type of cap, message preferences, language preferences, or the like.

The member data 120 may be accessed by various devices in the pharmacy, (e.g., the high volume fulfillment center, etc.), to obtain information utilized for fulfillment and shipping of prescription orders. In some implementations, an external order processing device operated by or on behalf of a member may have access to at least a portion of the member data 120 for review, verification, etc., or other purposes.

In some implementations, the member data 120 may include information for persons who are users of the pharmacy but are not members in the pharmacy benefit plan being provided by the PBM. For example, these users may obtain drug directly from the pharmacy, through a private label service offered by the pharmacy, the high volume fulfillment center, or otherwise. In general, the use of the terms member and user may be used interchangeably herein.

The claims data 122 includes information regarding pharmacy claims adjudicated by the PBM under a drug benefit program provided by the PBM for one, or more than one, plan sponsors. In general, the claims data 122 includes an identification of the client that sponsors the drug benefit program under which the claim is made, and/or the member that purchased the prescription drug giving rise to the claim, the prescription drug that was filled by the pharmacy (e.g., the national drug code number, etc.), the dispensing date, generic indicator, GPI number, medication class, the cost of the prescription drug provided under the drug benefit program, the copay/coinsurance amount, rebate information, and/or member eligibility, etc. Additional information may be included.

In some implementations, other types of claims beyond prescription drug claims may be stored in the claims data 122. For example, medical claims, dental claims, wellness claims, or other type of health care-related claims for members may be stored as a portion of the claims data 122.

In some implementations, the claims data 122 includes claims that identify the members with whom the claims are associated. In some implementations, the claims data 122 includes claims that have been de-identified (e.g., associated with a unique identifier but not with a particular, identifiable member, etc.).

The drug data 124 may include drug name (e.g., technical name and/or common name, etc.), other names by which the drug is known by, active ingredients, an image of the drug (e.g., in pill form, etc.), and the like. The drug data 124 may include information associated with a single medication or multiple medications.

The prescription data 126 may include information regarding prescriptions that may be issued by prescribers on behalf of users, who may be members of the pharmacy benefit plan, for example to be filled by a pharmacy. Examples of the prescription data 126 include user names, medication or treatment (such as lab tests), dosing information, and the like. The prescriptions may be electronic prescriptions, paper prescriptions that have been scanned, or otherwise. In some implementations, the dosing information reflects a frequency of use (e.g., once a day, twice a day, before each meal, etc.) and a duration of use (e.g., a few days, a week, a few weeks, a month, etc.).

In some implementations, the order data 118 may be linked to associated member data 120, claims data 122, drug data 124, and/or prescription data 126.

The plan sponsor data 128 includes information regarding the plan sponsors of the PBM. Examples of the plan sponsor data 128 include company name, company address, contact name, contact telephone number, contact e-mail address, etc., and the like.

Figure 2:
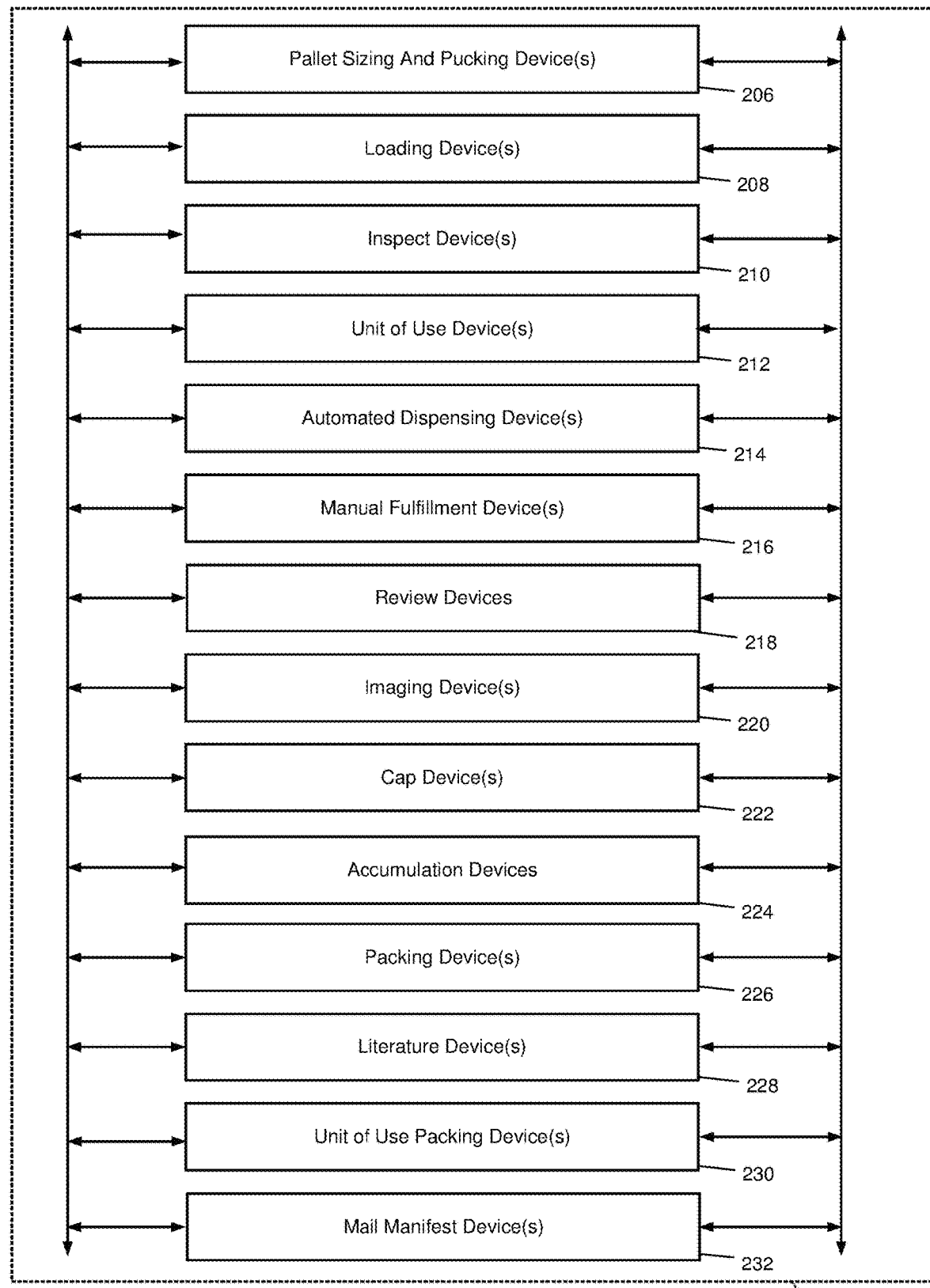
FIG. 2 is a functional block diagram of an example pharmacy fulfillment device, which may be deployed within the system of FIG. 1.

FIG. 2 illustrates the pharmacy fulfillment device 112, according to an example implementation. The pharmacy fulfillment device 112 may be used to process and fulfill prescriptions and prescription orders. After fulfillment, the fulfilled prescriptions are packed for shipping.

The pharmacy fulfillment device 112 may include devices in communication with the benefit manager device 102, the order processing device 114, and/or the storage device 110, directly or over the network 104. Specifically, the pharmacy fulfillment device 112 may include pallet sizing and pucking device(s) 206, loading device(s) 208, inspect device(s) 210, unit of use device(s) 212, automated dispensing device(s) 214, manual fulfillment device(s) 216, review devices 218, imaging device(s) 220, cap device(s) 222, accumulation devices 224, packing device(s) 226, literature device(s) 228, unit of use packing device(s) 230, and mail manifest device(s) 232. Further, the pharmacy fulfillment device 112 may include additional devices, which may communicate with each other directly or over the network 104.

In some implementations, operations performed by one of these devices 206-232 may be performed sequentially, or in parallel with the operations of another device as may be coordinated by the order processing device 114. In some implementations, the order processing device 114 tracks a prescription with the pharmacy based on operations performed by one or more than one devices 206-232.

In some implementations, the pharmacy fulfillment device 112 may transport prescription drug containers, for example, between more than one of the devices 206-232 in the high volume fulfillment center, by use of pallets. The pallet sizing and pucking device 206 may configure pucks in a pallet. A pallet may be a transport structure for a number of prescription containers, and may include a number of cavities. A puck may be placed in one or more than one of the cavities in a pallet by the pallet sizing and pucking device 206. The puck may include a receptacle sized and shaped to receive a prescription container. Such containers may be supported by the pucks during carriage in the pallet. Different pucks may have differently sized and shaped receptacles to accommodate containers of differing sizes, as may be appropriate for different prescriptions.

The arrangement of pucks in a pallet may be determined by the order processing device 114 based on prescriptions that the order processing device 114 decides to launch. The arrangement logic may be implemented directly in the pallet sizing and pucking device 206. Once a prescription is set to be launched, a puck suitable for the appropriate size of container for that prescription may be positioned in a pallet by a robotic arm or pickers. The pallet sizing and pucking device 206 may launch a pallet once pucks have been configured in the pallet.

The loading device 208 may load prescription containers into the pucks on a pallet by a robotic arm, a pick and place mechanism, or the like. In various implementations, the loading device 208 has robotic arms or pickers to grasp a prescription container and move it to and from a pallet or a puck. The loading device 208 may also print a label that is appropriate for a container that is to be loaded onto the pallet, and apply the label to the container. The pallet may be located on a conveyor assembly during these operations, (e.g., at the high volume fulfillment center, etc.).

The inspect device 210 may verify that containers in a pallet are correctly labeled and in the correct spot on the pallet. The inspect device 210 may scan the label on one or more than one containers on the pallet. Labels of containers may be scanned or imaged in full or in part by the inspect device 210. Such imaging may occur after the container has been lifted out of its puck by a robotic arm, picker, etc., or the like, or may be otherwise scanned or imaged while retained in the puck. In some implementations, images and/or video captured by the inspect device 210 may be stored in the storage device 110 as order data 118.

The unit of use device 212 may temporarily store, monitor, label and/or dispense unit of use products. In general, unit of use products are prescription drug products that may be delivered to a user or member without being repackaged at the pharmacy. These products may include pills in a container, pills in a blister pack, inhalers, and the like. Prescription drug products dispensed by the unit of use device 212 may be packaged individually or collectively for shipping, or may be shipped in combination with other prescription drugs dispensed by other devices in the high volume fulfillment center.

At least some of the operations of devices 206-232 may be directed by the order processing device 114. For example, the manual fulfillment device 216, the review device 218, the automated dispensing device 214, and/or the packing device 226, etc. may receive instructions provided by the order processing device 114.

The automated dispensing device 214 may include one or more than one devices that dispense prescription drugs or pharmaceuticals into prescription containers in accordance with one or multiple prescription orders. In general, the automated dispensing device 214 may include mechanical and electronic components with, in some implementations, software and/or logic to facilitate pharmaceutical dispensing that would otherwise be performed in a manual fashion by a pharmacist and/or pharmacist technician. For example, the automated dispensing device 214 may include high volume fillers that fill a number of prescription drug types at a rapid rate and blister pack machines that dispense and pack drugs into a blister pack. Prescription drugs dispensed by the automated dispensing devices 214 may be packaged individually or collectively for shipping, or may be shipped in combination with other prescription drugs dispensed by other devices in the high volume fulfillment center.

The manual fulfillment device 216 may provide for manual fulfillment of prescriptions. For example, the manual fulfillment device 216 may receive or obtain a container and enable fulfillment of the container by a pharmacist or pharmacy technician. In some implementations, the manual fulfillment device 216 provides the filled container to another device in the pharmacy fulfillment devices 112 to be joined with other containers in a prescription order for a user or member. In general, a manual fulfillment may include operations at least partially performed by a pharmacist or a pharmacy technician. For example, a person may retrieve a supply of the prescribed drug, may make an observation, may count out a prescribed quantity of drugs and place them into a prescription container, or the like. Some portions of the manual fulfillment process may be automated by use of a machine. For example, counting of capsules, tablets, or pills may be at least partially automated (e.g., through use of a pill counter, etc.). Prescription drugs dispensed by the manual fulfillment device 216 may be packaged individually or collectively for shipping, or may be shipped in combination with other prescription drugs dispensed by other devices in the high volume fulfillment center.

The review device 218 may process prescription containers to be reviewed by a pharmacist for proper pill count, exception handling, prescription verification, and the like. Fulfilled prescriptions may be manually reviewed and/or verified by a pharmacist, as may be required by state or local law. A pharmacist or other licensed pharmacy person who may dispense certain drugs in compliance with local and/or other laws may operate the review device 218 and visually inspect a prescription container that has been filled with a prescription drug. The pharmacist may review, verify, and/or evaluate drug quantity, drug strength, and/or drug interaction concerns, or otherwise perform pharmacist services. The pharmacist may also handle containers which have been flagged as an exception, such as containers with unreadable labels, containers for which the associated prescription order has been canceled, containers with defects, and the like. In an example, the manual review can be performed at the manual station.

The imaging device 220 may image containers once they have been filled with pharmaceuticals. The imaging device 220 may measure a fill height of the pharmaceuticals in the container based on the obtained image to determine if the container is filled to the correct height given the type of pharmaceutical and the number of pills in the prescription. Images of the pills in the container may also be obtained to detect the size of the pills themselves and markings thereon. The images may be transmitted to the order processing device 114, and/or stored in the storage device 110 as part of the order data 118.

The cap device 222 may be used to cap or otherwise seal a prescription container. In some implementations, the cap device 222 may secure a prescription container with a type of cap in accordance with a user preference (e.g., a preference regarding child resistance, etc.), a plan sponsor preference, a prescriber preference, or the like. The cap device 222 may also etch a message into the cap, although this process may be performed by a subsequent device in the high volume fulfillment center.

The accumulation device 224 accumulates various containers of prescription drugs in a prescription order. The accumulation device 224 may accumulate prescription containers from various devices or areas of the pharmacy. For example, the accumulation device 224 may accumulate prescription containers from the unit of use device 212, the automated dispensing device 214, the manual fulfillment device 216, and the review device 218, at the high volume fulfillment center. The accumulation device 224 may be used to group the prescription containers prior to shipment to the member or otherwise.

The literature device 228 prints, or otherwise generates, literature to include with prescription drug orders. The literature may be printed on multiple sheets of substrates, such as paper, coated paper, printable polymers, or combinations thereof. The literature printed by the literature device 228 may include information required to accompany the prescription drugs included in a prescription order, relating to prescription drugs in the order, financial information associated with the order (e.g., an invoice or an account statement, etc., or the like).

In some implementations, the literature device 228 folds or otherwise prepares the literature for inclusion with a prescription drug order (e.g., in a shipping container, etc.). In some implementations, the literature device 228 that prints the literature may be separate from the literature device that prepares the literature for inclusion with a prescription order.

The packing device 226 packages a prescription order in preparation for shipping the order. The packing device 226 may box, bag, or otherwise package the fulfilled prescription order for delivery. The packing device 226 may further place inserts, (e.g., literature or other papers, etc.), into the packaging received from the literature device 228 or otherwise. For example, bulk prescription orders may be shipped in a box, while other prescription orders may be shipped in a bag which may be a wrap seal bag.

The packing device 226 may label the box or bag with an address and a recipient's name. The label may be printed and affixed to the bag or box, be printed directly onto the bag or box, or otherwise associated with the bag or box, etc. The packing device 226 may sort the box or bag for mailing in an efficient manner (e.g., sort by delivery address, etc.). The packing device 226 may include ice or temperature sensitive elements for prescriptions which are to be kept within a temperature range during shipping in order to retain efficacy or otherwise. The ultimate package may then be shipped through postal mail, through a mail order delivery service that ships via ground and/or air (e.g., UPS, FEDEX, or DHL, etc.), through delivery service, through a locker box at a shipping site (e.g., AMAZON locker or a PO Box, etc.), or otherwise.

The unit of use packing device 230 packages a unit of use prescription order in preparation for shipping the order. The unit of use packing device 230 may include manual scanning of containers to be bagged for shipping to verify each container in the order. In an example implementation, the manual scanning may be performed at a manual station. The pharmacy fulfillment device 112 may also include a mail manifest device 232 to print mailing labels used by the packing device 226 and may print shipping manifests and packing lists.

While the pharmacy fulfillment device 112 in FIG. 2 is shown to include single devices 206-232, multiple devices may be used. The devices 206-232 may be the same type or model of device or may be different device types or models. When multiple devices are present, the multiple devices may be of the same device type or models or may be a different device type or model. The types of devices 206-232 shown in FIG. 2 are example devices. In other configurations of the system 100, lesser, additional, or different types of devices may be included.

Moreover, multiple devices may share processing and/or memory resources. The devices 206-232 may be located in the same area or in different locations. For example, the devices 206-232 may be located in a building or set of adjoining buildings. The devices 206-232 may be interconnected (e.g. by conveyors, etc.), networked, and/or otherwise in contact with one another or integrated with one another, (e.g., at the high volume fulfillment center, etc.). In addition, the functionality of a device may be split among a number of discrete devices and/or combined with other devices.

Figure 3:
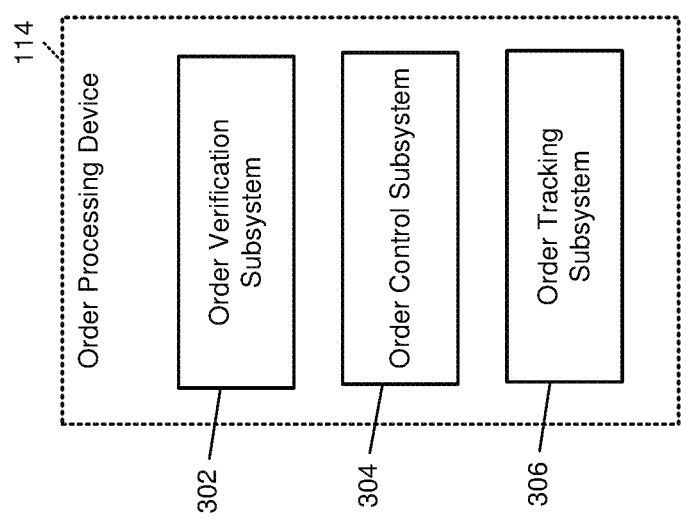
FIG. 3 is a functional block diagram of an example order processing device, which may be deployed within the system of FIG. 1.

FIG. 3 illustrates the order processing device 114, according to an example implementation. The order processing device 114 may be used by one or more than one operators to generate prescription orders, make routing decisions, make prescription order consolidation decisions, track literature with the system 100, and/or view order status and other order related information. For example, the prescription order may be comprised of order components.

The order processing device 114 may receive instructions to fulfill an order without operator intervention. An order component may include a prescription drug fulfilled by use of a container through the system 100. The order processing device 114 may include an order verification subsystem 302, an order control subsystem 304, and/or an order tracking subsystem 306. Other subsystems may also be included in the order processing device 114.

The order verification subsystem 302 may communicate with the benefit manager device 102 to verify the eligibility of the member and review the formulary to determine appropriate copayment, coinsurance, and deductible for the prescription drug and/or perform a DUR. Other communications between the order verification subsystem 302 and the benefit manager device 102 may be performed for a variety of purposes.

The order control subsystem 304 controls various movements of the containers and/or pallets along with various filling functions during their progression through the system 100. In some implementations, the order control subsystem 304 may identify the prescribed drug in one or more than one prescription orders as capable of being fulfilled by the automated dispensing device 214. The order control subsystem 304 may determine which prescriptions are to be launched and may determine that a pallet of automated-fill containers is to be launched.

The order control subsystem 304 may determine that an automated-fill prescription of a specific pharmaceutical is to be launched and may examine a queue of orders awaiting fulfillment for other prescription orders which will be filled with the same pharmaceutical. The order control subsystem 304 may then launch orders with similar automated-fill pharmaceutical needs together in a pallet to the automated dispensing device 214. As the devices 206-232 may be interconnected by a system of conveyors or other container movement systems, the order control subsystem 304 may control various conveyors to deliver the pallet from the loading device 208 to the manual fulfillment device 216, for example, from the literature device 228 to deliver paperwork as needed to fill the prescription.

The order tracking subsystem 306 may track a prescription order as it progresses (or stops) toward fulfillment. The order tracking subsystem 306 may track, record and/or update order history, order status, or the like. The order tracking subsystem 306 may store data locally (e.g., in a memory, etc.) or as a portion of the order data 118 stored in the storage device 110.

Block Diagrams

Figure 4:
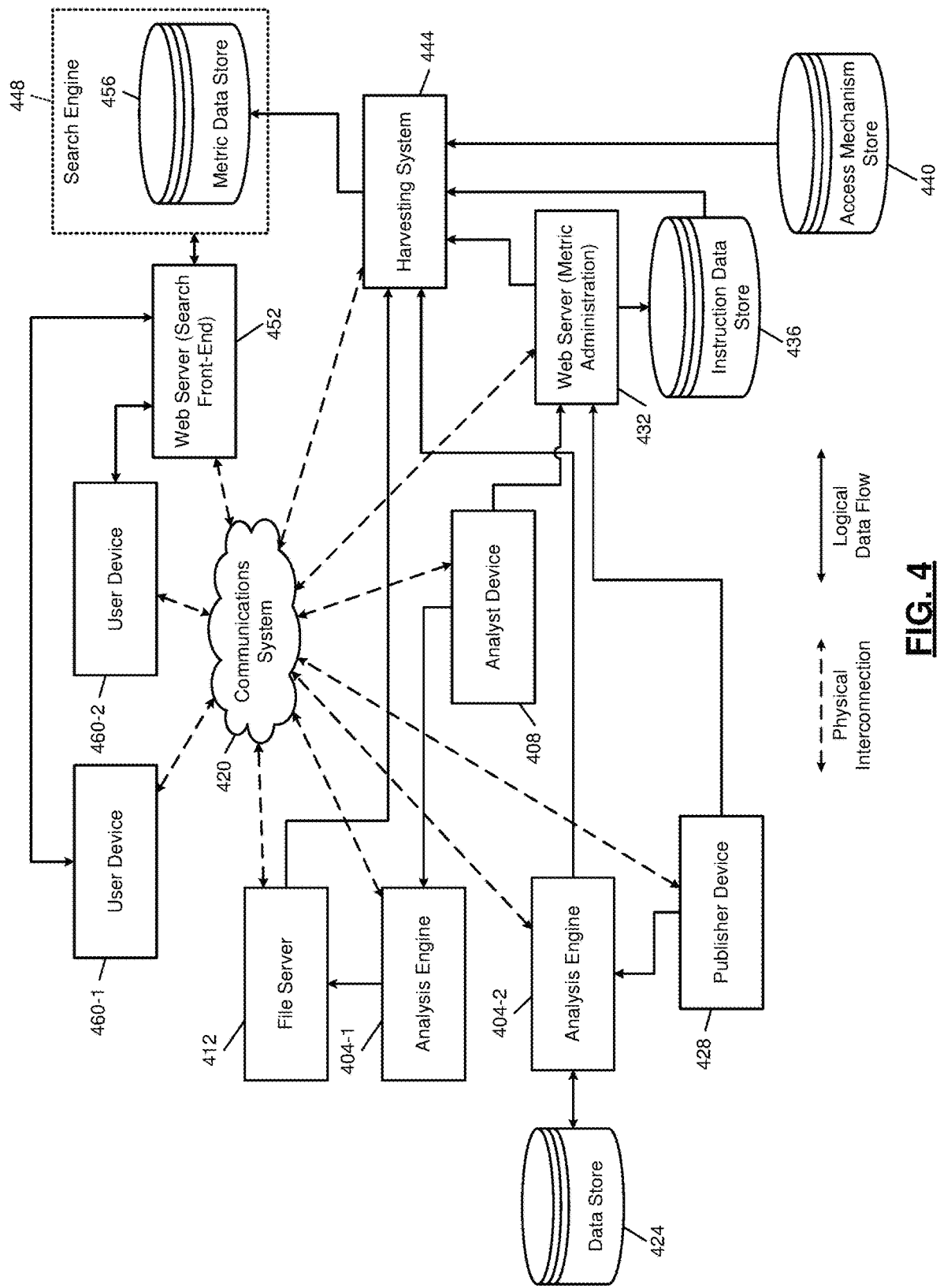
FIG. 4 is a functional block diagram of an example data analysis environment including a search system according to the principles of the present disclosure.

In FIG. 4, an example environment in which the principles of the present disclosure can be implemented includes analysis engines 404-1 and 404-2 (collectively, analysis engines 404). Although two analysis engine are shown in FIG. 4, the present disclosure is equally applicable to a single analysis engine as well as to more than two analysis engines. Each of the analysis engines 404 may include a client computing device or a server computing device that may execute database software, business intelligence (BI) software, and/or custom analysis software.

In various implementations, the analysis engines 404 may be operated for the benefit of a single organization, such as a corporation. The analysis engines 404 may be operated wholly or partially on equipment owned by the organization, which may be located on premises owned by the organization or on premises provided by a third party. In various implementations, one or both of the analysis engines 404 may be operated and hosted by a third party. For example, the analysis engine 404-1 may be a software-as-a-service offering from a third party that operates on the third party's servers and uses the organization's data.

An analyst device 408, which may include a laptop or desktop computer under the control of an analyst, controls the analysis engine 404-1. For example, the analyst device 408 may establish a database schema, configure parameters for extract, transform, and load (ETL) procedures, etc. The analyst device 408 may configure data processing by the analysis engine 404-1 that results in the generation of one or more metrics.

These metrics may be outputted, such as to files on a file server 412. For example, the metrics may be outputted as a text-based file, such as a comma separated value (CSV) file. In other configurations, the file server 412 may host proprietary file formats such as spreadsheet or database files. These files may be outputted by the analysis engine 404-1 or may store data for use by the analysis engine 404-1. In some configurations, certain files on the file server 412 are reserved for output, such as of metrics. In other configurations, files on the file server 412 may combine metrics with input and intermediate data for use by the analysis engine 404-1.

Although solid lines are shown in FIG. 4 to indicate logical data flow among elements, actual communication between these elements may be indirect. For example, the elements may communicate with each other via a communications system 420. Because the exact physical interconnection is not central to the disclosure, the physical interconnections are shown in dashed lines and omitted in future figures.

The analysis engine 404-2 interfaces with a data store 424, which may be the backend for a relational database or a NoSQL database. A publisher device 428 is a computing device under the control of a publisher who is responsible for making the results of analysis available to other users. In various implementations, the publisher may be the same as the analyst who created the data or their roles may be separate. An analyst may have developed a structured query language (SQL) query to run on the analysis engine 404-2 that results in a metric.

Via the publisher device 428, the publisher may publish the SQL query to a search system according to the principles of the present disclosure. As an example implementation only, the search system includes a web server 432 used for administration and onboarding of metrics, an instruction data store 436, an access mechanism store 440, a harvesting system 444, a search engine 448, and a web server 452 accessed by users. In various implementations, the web server 432 and the web server 452 may be implemented by a common web server architecture, such as an Nginx web server from Nginx, Inc., and may simply be two different pages served from the common web server architecture.

The web server 432 presents an administrative interface that allows the publisher, via the publisher device 428, to specify the SQL query and indicate how to identify a particular metric from the result of the SQL query. In addition, the publisher may provide metadata to the web server 432 about the metric. For example, this metadata may include a schedule for when the metric is updated. Updates may occur on a strictly periodic basis or according to a calendar, or may only occur in response to certain events.

The publisher may provide a textual description of the metric in full sentence form as well as a short form text description. The publisher may also provide a set of tags by which the metric can be indexed. The publisher device 428 may indicate an identity of the analyst or analysis team that generated the SQL query. The publisher may provide contact information for the publisher as well as the analyst to allow consumers of the metric to request additional information regarding the metric or to request similar metrics. The publisher may also assign a confidence score to the metric indicating the degree to which the metric is authoritative. The confidence score may also indicate the degree to which the publisher is confident that the metric will remain valid over time.

The publisher may specify access rights for the metric. As one example, the access rights may be co-extensive with the access rights to the analysis engine 404-2 or the data store 424. In other scenarios, the publisher may provide wider access to the metric than is available for the underlying data. In various implementations, the search system may identify what access rights apply to a metric and then automatically restrict disclosure of that metric to users having the same access rights.

In various implementations, some or all of the information provided by the publisher/analyst may be stored within the metric source itself rather than being provided to the instruction data store 436. For example, the publisher may simply provide the web server 432 with a location of a metric and an update schedule. According to the update schedule, the harvesting system 444 can access the source of the metric at the specified location and obtain the remaining data, such as text description, keywords, access rights, etc. In this way, an analyst can update the metric metadata without needing to use the web server 432 or even having access rights to the web server 432.

Meanwhile, via the analyst device 408, the analyst may provide similar metric information to the web server 432 with respect to a metric available from the analysis engine 404-1. Although the illustration in FIG. 4 depicts a single analyst device (408) communicating with a single analysis engine (404-1) and a single publisher device (428) communicating with another analysis engine (404-2), there is nothing to restrict analyst or publisher devices from communicating with multiple analysis engines. In other words, a publisher, using a publisher device, may publish multiple metrics from across a variety of analysis engines. Similarly, an analyst, using an analyst device, may perform analysis using a variety of analysis engines as well as publish metrics from a variety of analysis engines.

The web server 432 stores the metric information provided by the publisher into the instruction data store 436. For example only, the instruction data store 436 may be implemented using a PostgreSQL database system from the PostgreSQL Global Development Group. The harvesting system 444, as described in more detail below, uses instructions from the instruction data store 436—such as a uniform resource locator (URL) or a SQL query—to obtain values of the metrics according to the schedule specified in the instruction data store 436.

The harvesting system 444 is configured with access mechanisms defining how to access metrics from across a wide array of source data. These access mechanisms may be stored in the access mechanism store 440. For example, the access mechanism store 440 may include parsing routines configured to extract data from various files, such as standardized or proprietary spreadsheet formats, text-based formats (such as CSV or XML), word processing documents, publishing documents (such as PDFs), etc.

The access mechanism store 440 may also include access mechanisms, such as a library or executable, configured to obtain information from business intelligence (BI) software using an application programming interface (API). In other implementations, the access mechanism store 440 may access an API that causes the BI software to export certain data, such as to a text file on a file server. The access mechanism store 440 may also store access mechanisms configured to submit and receive responses to SQL queries. The access mechanism store 440 may also include libraries for accessing online resources, such as web pages or SHAREPOINT collaboration site documents.

Further, the access mechanism store 440 may include authentication information, such as authentication tokens, that authorize the harvesting system 444 to access various systems such as file servers and databases. In various implementations, the access mechanism store 440 may be maintained by an administrator of the search system. Additionally or alternatively, analysts and publishers may use the web server 432 to provide access mechanism information to the access mechanism store 440. For example, a publisher may create access credentials to a database and provide those credentials to the access mechanism store 440 for ongoing access to the database.

As the harvesting system 444 acquires metric information according to the instruction data store 436, the harvesting system 444 stores acquired metrics into a metric data store 456 of the search engine 448. In various implementations, the search engine 448 may index data received from the harvesting system 444 and store only these indices in the metric data store 456. In other words, the indices themselves store data and are not simply an index of a separate repository of metrics. The metric data store 456 may encrypt some or all metric values—particularly, personally identifiable information, patient information, and financial data.

The search engine 448 provides information from the metric data store 456 upon request. For example, users may find a web interface most convenient and therefore a web server 452 provides a front-end to the search engine 448. The web server 452 receives queries, such as from user devices 460-1 and 460-2 (collectively, user devices 460). The web server 452 provides information to the search engine 448 regarding the queries and presents results to the user devices 460.

The web server 452 may enforce access controls for the user devices 460, and may therefore require authentication by the user devices 460. In various implementations, certain data may be publicly accessible to any devices that are able to communicate with the web server 452. Therefore, the user devices 460 may only need to authenticate to the web server 452 to obtain data having more restricted access rights.

The web server 452 may display the most recent metric value for each of the search results. In various implementations, each of the user devices 460 may be able to configure the web server 452 to automatically provide additional historical metrics immediately or only after requesting historical data. As described above, the web server 452 may provide text descriptions of all relevant search results regardless of access rights but restrict display of the metric values to those having sufficient access rights. In addition, access rights may be more granular than simply by metric. For example, access rights may specify that a user can see the most recent value for a metric but not all of the historical values.

The web server 452 may also display, either immediately or upon a request for additional data, metadata associated with metrics, such as update time and source contact information. In addition, the web server 452 may allow the user devices 460 to quickly obtain access to the underlying source location or document. As an example, this may take the form of a hyperlink to a web server, file system, etc.

The web server 452 may receive information from the user devices 460, such as whether associated users of the user devices 460 believe a certain metric to be authoritative and/or helpful. This feedback may be displayed for other users to make value judgments about a metric. The web server 452 may also be configured to visually identify metrics that have been confirmed as authoritative, such as with a certain icon or changes in font formatting, such as application of a bold font face. In various implementations, the web server 452 may be configured authoritative metrics more highly.

Figure 5:
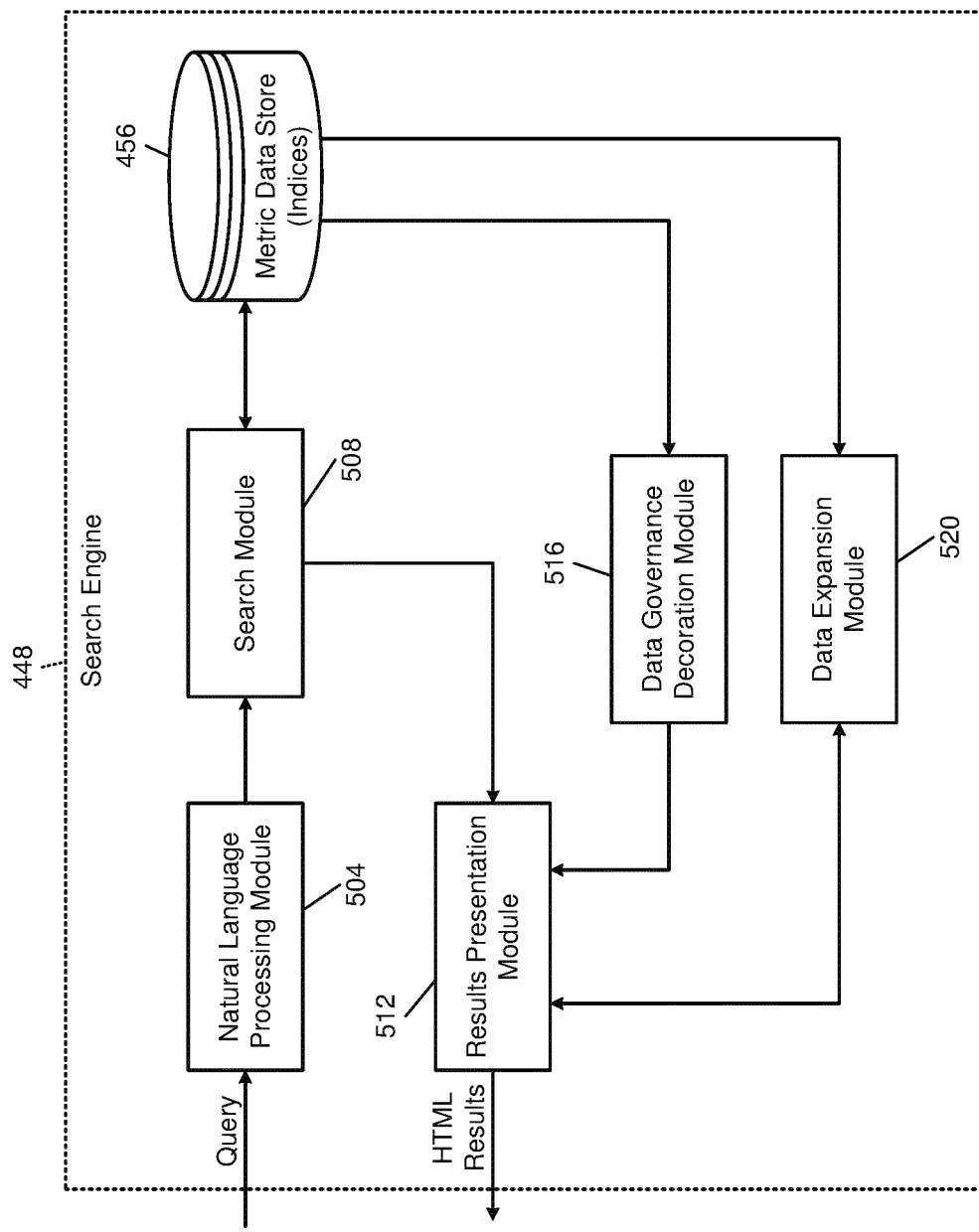
FIG. 5 is a functional block diagram of an example implementation of a search engine.

FIG. 5 presents elements of an example implementation of the search engine 448. A natural language processing module 504 receives a query, such as from the web server 452 of FIG. 4. Natural language processing module 504 determines a user intent and provides text tokens related to the user intent to a search module 508. As an example, the search module 508 may be implemented using the APACHE LUCENE information retrieval library from the Apache Software Foundation. The natural language processing module 504 may be implemented using the query parser of the Apache Lucene information retrieval library, which breaks a query into single terms, phrases, and operators.

The search module 508 identifies metrics from the metric data store 456 according to the tokens from the natural language processing module 504. For example, the tokens may be compared to keywords and text associated with the metrics in the metric data store 456. In some implementations, these keywords and text may be obtained from the instruction data store 436. In other implementations, these keywords and text are obtained from the source of the metric and stored into the metric data store 456.

A single set of metadata may apply to all values of a metric over time; or, taking into account that the metadata may change over time, metadata may be stored with each value of the metric. As an implementation detail, the metric data store 456 may use a compression scheme (for example, similar to run length encoding) so that multiple copies of identical metadata do not need to be saved with each metric acquired.

A results presentation module 512 generates hypertext markup language (HTML) results based on metrics obtained by the search module 508. These results include information about the metric as well as the metric itself. In addition, the results presentation module 512 may visually identify metrics determined to be authoritative by a data governance decoration module 516. The data governance decoration module 516 may rely on information from the metric data store 456 specified by publishers and/or data governance specialists.

A data expansion module 520 may select a single value of the metric for the results presentation module 512—generally, the most recent value of the metric—with the ability to expand to additional values of the metric. For example, the data expansion module 520 may construct a line chart or bar chart of historical values of the metric in response to a request from a user for additional data.

The results presentation module 512 may initially provide a textual description of the metric along with the value for the metric. Upon user selection of metric, additional data may be displayed, such as a reference to the source data and contact information for the analyst or publisher, which may allow a direct email, call, or messaging platform communication to be initiated by the user.

Figure 6:
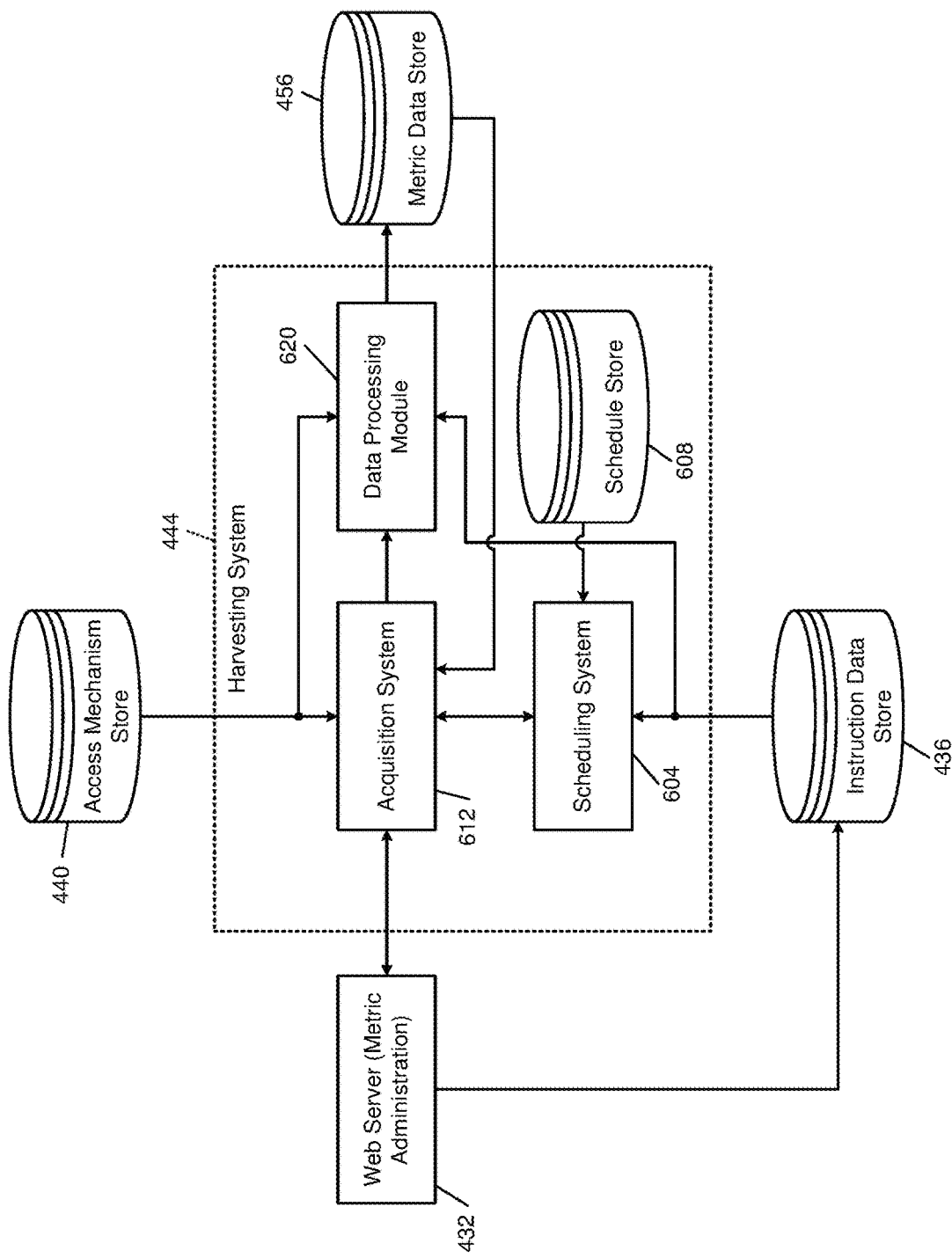
FIG. 6 is a functional block diagram of an example implementation of a harvesting system.

In FIG. 6, an example implementation of the harvesting system 444 includes a scheduling system 604 that determines, for each metric, when to check for a new value of the metric. The scheduling system 604 relies on information from the instruction data store 436 and may use schedules defined in a schedule store 608. For example, the schedule store 608 may encode schedules such as the first Monday of the month, the last Friday of the month, the first and 15th of each month, etc.

Upon request by the scheduling system 604, an acquisition system 612 attempts to obtain the metric specified by the instruction data store 436. For example, the acquisition system 612 may communicate with a file server, a database, an online resource (such as a SharePoint collaboration server from Microsoft Corporation) to obtain the metric.

In various implementations, the acquisition system 612 may first check to determine whether a modification date is more recent than the time at which the prior value of the metric was obtained. For example, the access mechanism store 440 may specify whether and how to determine a modification date. For example, an operating system may maintain a modification date for each file in the file system. If that modification date is not newer than the prior acquisition time of the metric, the acquisition system 612 may skip obtaining the metric.

In other implementations, the data source may encode the modification date in a response, such as to a SQL query or API call. However, if obtaining the modification date will require as much processing power and create the same amount of latency as simply obtaining the metric directly, checking the modification date may be avoided.

In various implementations, the publisher may specify that the metric be obtained regardless of whether the date or data has changed. For example, the operating system modification date may be inaccurate or unreliable. In another example, the source of a metric may update an output file only when the value of the metric changes. Therefore, even though the metric value has not changed and the modification date has not been updated, this represents a new value of the metric that should be indexed and presented to users.

Once data (such as the results of a SQL query) or a file is obtained by the acquisition system 612, a data processing module 620 may parse the data or file to extract the metric. This metric value is then provided to the metric data store 456. The data processing module 620 may operate under the control of the access mechanism store 440, which may specify parsing routines for various file types.

The instruction data store 436 or the data source itself may specify locations of metrics within a particular file or data set. As one example only, a particular cell of a spreadsheet may contain a metric of interest. Therefore, using a parsing routine from the access mechanism store 440, the data processing module 620 can extract the contents of a cell specified by the instruction data store 436 from a spreadsheet file obtained by the acquisition system 612.

When information about specific locations of data within a document or data set is encoded within that document or data set itself, the instruction data store 436 does not need to be updated to reflect changed locations. This may allow an analyst to, for example, revise a spreadsheet and simply update the spreadsheet accordingly. Continuing the spreadsheet example, a new location or tab of the spreadsheet may define, for each metric contained within that spreadsheet, where the metric can be found. In other implementations, that location or tab of the spreadsheet may actually contain a cell that is dynamically updated with the value of the metric. For example, the cell may include a formula that obtains the metric from another location in the spreadsheet. In this way, the predetermined location or tab of the spreadsheet will include a copy of the metric value, regardless of where that value is produced in the remainder of the spreadsheet. Then, as the analyst updates the spreadsheet, the analyst simply updates the formula of the cell to load the metric from its new location.

As a more specific example, the search system may define a specific tab name to be used for publishing metrics of spreadsheets. For a spreadsheet including a metric to be published, this tab is added to the spreadsheet by the analyst or publisher. Each row of this tab may corresponds to a different metric, with the potential exception of a predefined header row that is ignored by the acquisition system 612.

One column includes a value of the metric, while another column may specify units of the metric, which may simply be stored as text for presentation to users. In no particular order, another column includes the date or timestamp when the data was last refreshed. The format of this column may be predefined and require a specific time zone or a particular time standard such as Coordinated Universal Time (UTC). Another column specifies the name of the author (such as analyst) of the metric, while yet another column specifies contact information (such as email address) of the author.

Another column defines the metric in text form, which may be a longer form description, such as one or more full sentences. Another column specifies the name of the metric, which may be relatively standardized across analysts and may use shorthand for brevity. Another column defines keywords for the metric, which may conform to a specified format, such as being separated by a predefined delimiter.

Another column defines how frequently the data is refreshed. This call may be used by the scheduling system 604 to determine when to re-harvest the metric. In this way, the schedule may be updated anytime the metric is obtained. In other implementations, the refresh cadence column may simply be used as information to present to users of the search system, while the acquisition schedule is controlled explicitly by the publisher or author via the web server 432.

Another column specifies where the current file can be accessed, such as with a uniform resource locator (URL). The values in this column may be identical to the location of the spreadsheet used for access by the harvesting system 444. In other implementations, the harvesting system 444 may be accessing the spreadsheet via an alternative path, mounted drive, etc. Therefore, the source URL may be a more generally applicable location accessible by users.

In various implementations, some or all of these columns may be omitted. If a column is omitted, this data may be provided by the publisher explicitly to the web server 432 or may be omitted from the search system entirely. The only required column is the column including the metric value. As mentioned above, a cell in the metric value column may include a formula that obtains the value from another location or locations in the spreadsheet. In other implementations, the value column may specify where in the spreadsheet the value can be obtained, such as by sheet name, row identifier, and column identifier. In various implementations, similar metrics (for example, the same measurement made over different periods of time, such as a weekly value and a monthly value) are treated as separate metrics and therefore require separate rows.

If data is available in an online source, such as a SharePoint collaboration site from Microsoft Corporation), a list may be defined having columns similar to those described for a spreadsheet. This list may be hidden from view for regular users of the SharePoint collaboration site. The harvesting system 444 may be able to directly access the SharePoint list, such as using a URL pointing to the SharePoint list.

Business intelligence (BI) software (such as Tableau from Tableau Software) may be configured to output metrics via an API or to a file using a predetermined format. For example, the BI software may be configured to export metric data to a comma separated value (CSV) file each time the underlying data changes or upon request by the harvesting system 444. Data similar to the above columns for a spreadsheet may be manually programmed into the BI software and configured to export along with the metric values. As an example only, one approach to adapting Tableau BI software for the harvesting system 444 of the present disclosure is described in detail here.

Bisoftware Onboarding Example

In this example, consider a Tableau workbook called "Gym Utilization" that tracks visits to a hypothetical fitness facility. The workbook has several views, including peak hours of use and peak days of use. The main measure in the workbook is number of visits, with dates and times as dimensions. In this example, the publisher decides to publish the hours and days of most use and least use.

First, the publisher determines the exact data points to publish. For example, these may be: Hour of Most Visits, Hour of Fewest Visits, Day of Most Visits, Day of Least Visits, and four corresponding Visit Counts. A more complex representation of the data could use a calculated field rather than a single value.

Next, the publisher develops names and definitions that are complete and concise for each data point. For example, these may be:

a. Most popular hour of the day for gym usage in prior month
b. Most number of gym visits per hour in prior month
c. Least popular hour of the day for gym usage in prior month
d. Fewest number of gym visits per hour in prior month
e. Most popular day of the week for gym visits in prior month
f. Average gym visits on most popular day of the week in prior month
g. Least popular day of the week for gym visits in prior month
h. Average gym visits on least popular day of the week in prior month Next, the publisher identifies the author/analyst and analyst email for inclusion with these data points. As an example, the author may be designated as Shun Li, whose email address is shun_li@thepoet.com.

The publisher may then tag the data points with keywords, which may be used for cataloging and searching. The keywords do not need to repeat terms from the metric definitions, which will already be indexed. For this example, the keywords will be health, fitness, and exercise.

The publisher then identifies the cadence of the data refresh for the source of the data point. For example, this gym usage workbook may update on the first Monday of the month at approximately 0400 Central Standard Time.

To obtain a CSV version of a Tableau view, the publisher opens the view on the server using a web browser. The publisher then modifies the URL in the address bar by replacing the "?" and any subsequent characters with ".csv". The publisher then requests the CSV file by pressing return or clicking/tapping the browser's "Go" button. The publisher is then prompted to open or save the CSV file.

The CSV may be sorted by average visits, with row 1 being a header row and fourteen data points (rows 2-15). As an example, assume that the second column contains the average visit numbers. Therefore, the data points for greatest and fewest visit can be obtained from rows 2 and 15 of column 2 of the CSV.

However, the publisher should consider whether a different sort order may apply that will change the row for the data point. Further, the publisher should consider whether the data in question always appears in the view, such as when the value is <NULL>. Further, the publisher should consider whether the data relies on filter settings or parameters that could change due to data changes. If the location of the data points may change in the output file, the publisher might duplicate the view in a separate tab of the Tableau view and make appropriate adjustments to filters or view construction. As another option, the publisher may programmatically calculate the row number each time the data is updated. This row number would then need to be acquired by the harvesting system to determine from which row to obtain the metric value.

To prepare the Tableau workbook for harvesting, the publisher opens the workbook in the desktop Tableau application and navigates to the view with the data. For this example, the search system is named FAST (Frequently Asked STatistics) and therefore predefined names will be prefaced with "FAST". The publisher creates calculated fields with names "Author", "Author Email", "FASTMetric", "FASTTags", and "Refresh Cadence". In various implementations, the field names are case-sensitive.

The publisher then edits the Author and Author Email fields to reflect the author and/or subject matter expert for this data. The publisher edits the Refresh Cadence field to reflect the schedule of data refresh. The publisher edits the FASTTags field to insert terms delimited with semicolons and no other delimiters, such as spaces or commas.

The publisher edits the FASTMetric field to reflect the location of the data point in the CSV grid and a description of the data point. Each row of the FASTMetric field corresponds to one metric to be published. Each item in the row is separated by a semicolon. The FASTMetric field can be constructed as follows:

a. Type a double quote (").
b. Type or copy/paste the name of the column header of the data from the CSV file exactly as it is displayed in the CSV file, followed by a semicolon.
c. Type the number of the row for the data (row 1 contains the column headers) followed by a semicolon.
d. Type the desired Display Name for the data point (this may be the same as the column header) followed by a semicolon.
e. Type the Definition/Comments/Other information about the data followed by a semicolon. This provides context for the data as it will appear by itself in a search result.
f. Avoid special characters such as "{ }\; unless specifically instructed.
g. Hit <Return>.
h. Repeat steps b through g for each data point to harvest. Each data point can have different columns and rows.
i. Type a closing double quote (").

When constructed as above for the four metrics in the current Tableau view, the FASTMetric field is as follows: "Hour of In;2;Gym Visit Start Time;Most popular hour of day for Gym usage; Avg Visits;2;Number of Gym Visits per hour;Most Number of Visits per hour; Hour of In;15;Gym Visit Start Time;Least popular hour of day for Gym usage; Avg Visits;15;Number of Gym Visits per hour;Least Number of visits per hour"

Note that the first entry is the column header from the CSV file that contains the data point. The next entry is the row number (2 or 15). The next entry is a display name for the data point, and the last entry is the description. The four lines in the FASTMetric field correspond to the four separate data points. Add each of the created fields to the details card of the Tableau view. They can be eliminated from the tooltip without affecting harvesting. This view is then ready for harvesting.

Consider another view for this fitness facility workbook. This view contains average number of gym visits by day of the week and can therefore be used to determine the most and least popular days of the week for gym visits in the prior month. The CSV output file may include a column for day of the week and a column for average number of gym visits, with the data sorted by day of the week. As a result, the row that contains the most visits is not always the same, and neither is the row that contains the fewest visits.

To address this issue, the publisher creates a duplicate view and changes the sort order to number of visits instead of days of the week. For example, the duplicate worksheet can be named FAST_DayOfWeek. The sort order in the FAST_DayOfWeek worksheet is set to number of visits in descending order. Then, the CSV output file for the FAST_DayOfWeek worksheet will (assuming visits are tracked from Monday-Friday and not on the weekends), include a header row and five weekday rows, with the greatest number of visits being in row 2 and the fewest number of visits being in row 6.

The FASTMetric field (this one may be titled FASTMetric2 to differentiate from the FASTMetric field in the other view) can be constructed as follows:

"Day of the Week;2;Day of the Week;Most popular day of the week for Gym Visits
Avg Visits (copy);2;Average Gym Visits;Number of Average Visits to the Gym on most popular day of the week
Day of the Week;6;Day of the Week;Least popular day of the week for Gym Visits
Avg Visits (copy);6;Average Gym Visits;Number of Average Visits to the Gym on least popular day of the week"

Now the workbook with the FAST_DayOfWeek worksheet is published and the CSV URL is provided to the web server 432. The harvesting system can then review FASTMetric* fields from the URL to determine how to obtain metric values.

Some idiosyncrasies to keep in mind are that Tableau exports CSV files with column headings sorted left to right with an alphabetical sort of Dimensions and Measures that are created within Tableau Desktop, such as Calculated Fields, Groups, and Sets. Then, Tableau lists the remaining Dimensions and Measures from the data source in alphabetical order.

Calculated fields are used to perform row sort before any other dimensions and only are sorted on their value (even if the sort is set to another field, this won't be reflected in the CSV). This property may be used to create a specific row sort order. For example, make the calculated field value represent the desired sort order and label it starting with an underscore: for example, as in "_Counts". This will make sure it is first in the column list and therefore be the sort of the CSV file.

Flowcharts

Figure 7:
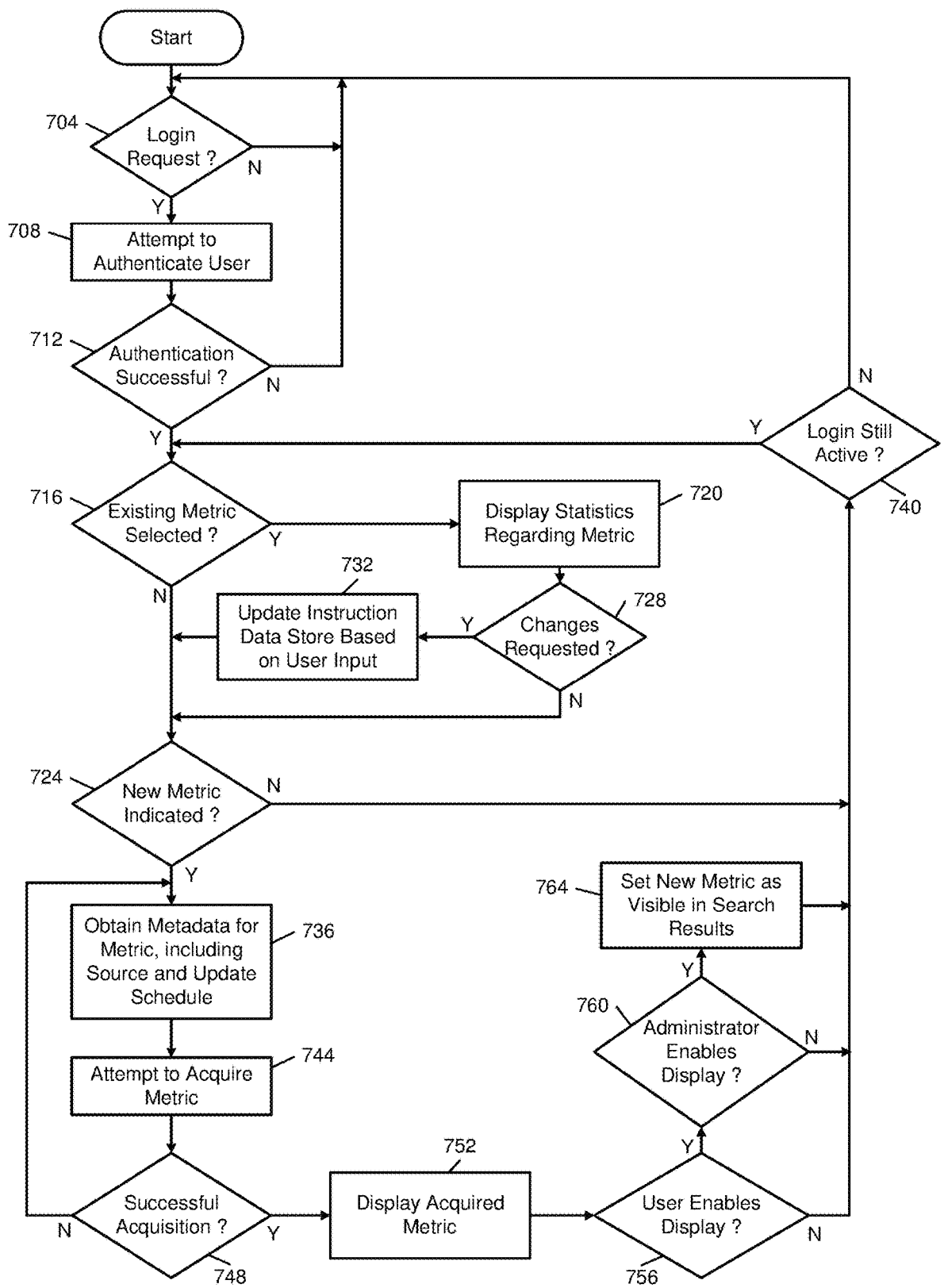
FIG. 7 is a flowchart of example operation of the administrative frontend for the harvesting system.

In FIG. 7, example operation of an administrative interface (such as presented by the web server 452) for publishers and analysts begins at 704. If a login request is made by a user, control transfers to 708; otherwise, control remains at 704. At 708, control attempts to authenticate the user. At 712, if authentication was successful, control transfers to 716; otherwise, control returns to 704. For example only, authentication may be based on an Active Directory identity system from Microsoft Corporation or may rely on tokens generated by a single-sign-on process.

At 716, if an existing metric is selected by a user, control transfers to 720; otherwise, control transfers to 724. At 720, control displays just statistics regarding the metric. At 728, control determines whether changes have been requested by the user. If so, control transfers to 732; otherwise, control transfers to 724. At 732, control updates the instruction data store based on the user input. For example, the location of the metric may have changed and therefore the user provides a new URL.

At 724, control determines whether the user has indicated an intent to publish a new metric. If so, control transfers to 736; otherwise, control transfers to 740. At 740, control determines whether the login is still active. If so, control transfers to 716; otherwise, control returns to 704. At 736, control obtains metadata for the metric, including the source (such as the URL) and an update schedule. Control may also acquire additional metadata regarding the metric.

At 744, control attempts to acquire the metric based on the specified source. At 748, if acquisition was successful, control transfers to 752; otherwise, control returns to 736 to request corrected metadata. At 752, control displays the acquired metric to the user for confirmation. At 756, control determines whether the user has instructed enabling the metric to be displayed. For example, the user may desire to have the search engine begin acquiring the metric before displaying the metric to users. If the user decides to enable the display, control transfers to 760; otherwise, control transfers to 740.

At 760, in the case an administrator is required to approve new metrics, the administrator may review the metric provided by the user. Although shown immediately after 756, administrator review may happen asynchronously, such as in response to an alert of a new metric, or daily. At 760, if the administrator enables display of the metric, control transfers to 764; otherwise, control transfers to 740. At 764, control sets the new metric as visible in search results, allowing the metric to be presented to users in response to queries. Control then returns to 740.

Figure 8:
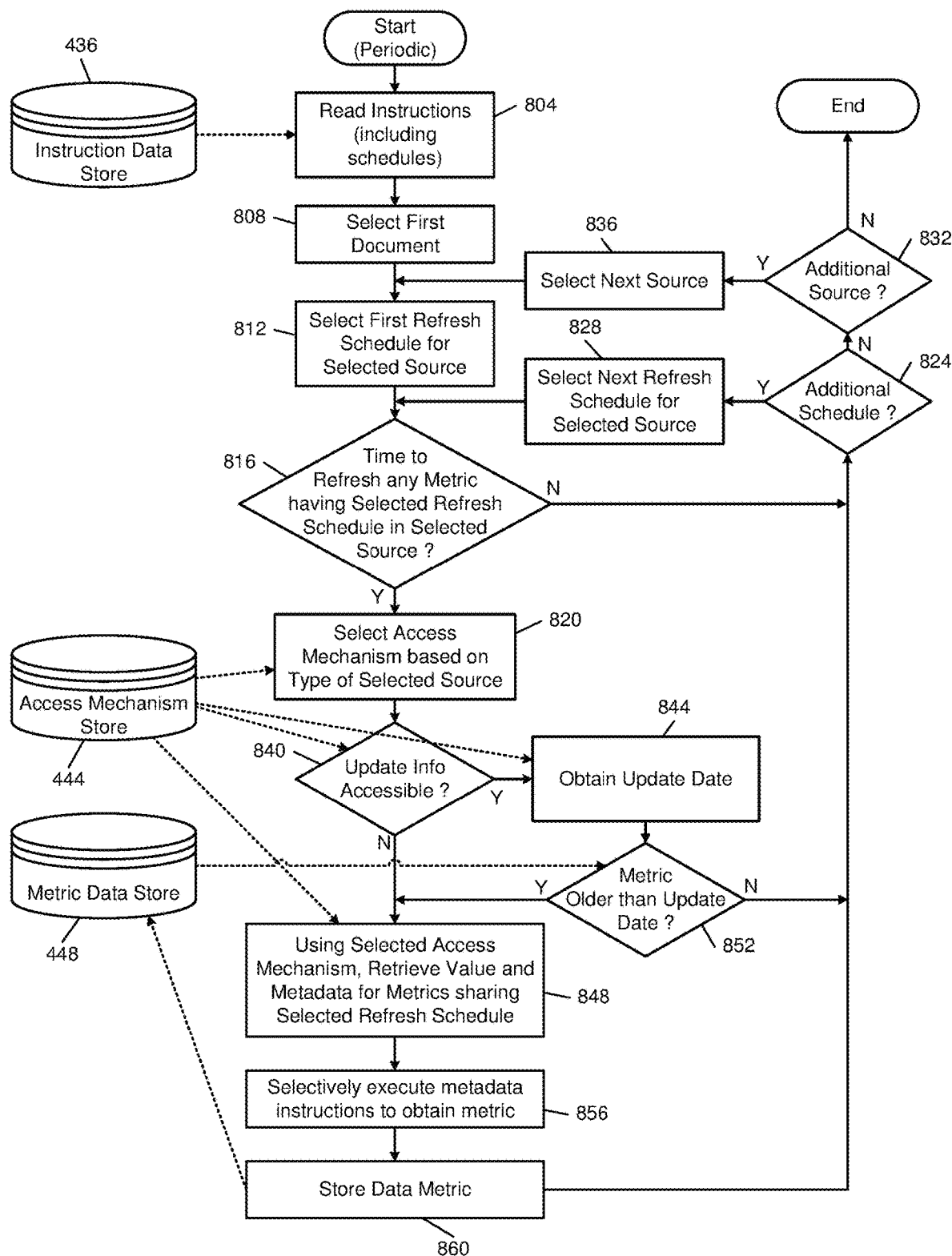
FIG. 8 is a flowchart of example operation of the harvesting system.

In FIG. 8, example operation of the harvesting system 444 begins at 804. For example, control may begin on a periodic schedule, such as once per second. At 804, control reads instructions, including schedules, from the instruction data store 436. At 808, control selects the first metric source. At 812, control identifies all of the refresh schedules pertinent to the selected document source and selects the first of those refresh schedules.

At 816, control determines whether it is time to refresh any data from the selected source having the selected schedule. For example, if any metric was obtained prior to the most recent event in the selected refresh schedule, that metric is eligible for reacquisition. If any metric is potentially out of date based on the selected refresh schedule, control transfers to 820; otherwise, control transfers to 824. At 824, control determines whether there are any additional schedules pertinent to the selected data source. If so, control transfers to 828; otherwise, control transfers to 832. At 828, control selects the next refresh schedule applicable to the selected metric source and continues at 816. At 832, control determines whether there are any additional metric sources specified by the instruction data store 436. If so, control transfers to 836; otherwise, control ends. At 836, control selects the next metric source and continues at 812.

At 820, control selects an access mechanism based on the type of the selected metric source. These access mechanisms may be maintained by the access mechanism store 440. For example, the access mechanism may permit submission of a SQL query or access to a SharePoint collaboration site list object. The access mechanism store 440 may also specify how to obtain modification date information. At 840, if the access mechanism store 440 indicates that modification date information is potentially available, control transfers to 844; otherwise, control transfers to 848. At 844, control obtains the modification date for the metric using the selected access mechanism. Control then continues at 852. If the most recent value of any metric is older than the update date, control transfers to 848; otherwise, control transfers to 824.

At 848, using the selected access mechanism, control attempts to retrieve values and metadata for metrics sharing the selected refresh schedule from the selected metric source. In response to an error, such as predefined names not being present in the selected metric source, control may signal an error to an administrator of the search system and return to 824.

At 856, control may execute instructions indicated by the metadata, such as accessing a particular cell within the spreadsheet. As an example, a predefined location within a spreadsheet may include a row for each metric, where that row indicates a location of the metric value throughout the spreadsheet. At 860, control stores the obtained metric data into the metric data store 456. Control then continues at 824.

CONCLUSION

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. An administrative interface configured to be used with one or more databases for analytics comprising:
   specifying, via the administrative interface, a first predefined label for use with the one or more databases for analytics;
   receiving a first input designating a first location of a first analytic;
   obtaining a first document from the first location;
   identifying the first predefined label within the first document;
   obtaining a first datum associated with the first predefined label from the first document;
   storing the first datum into a value index as a current value of the first analytic;
   obtaining a second datum associated with the first predefined label from the first document;
   storing the second datum into a text index as a textual description of the first analytic; and
   determining a level of authority to associate with the first analytic.

2. The administrative interface of claim 1, wherein determining a level of authority to associate with the first analytic comprises:
   in response to obtaining the first document, acquiring, from a predefined position in the first document with respect to the first predefined label, identification information for one or more of an author and a publisher of the first analytic;
   acquiring credibility data associated with the one or more of the author and the publisher of the first analytic;

determining a credibility value to associate with the first analytic based, at least in part, on the acquired credibility data; and utilizing the credibility value, at least in part, to determine the level of authority to associate with the first analytic.

3. The administrative interface of claim 2, further comprising:

selectively displaying the identification information for one or more of the author and a publisher of the first analytic to a user.

4. The administrative interface of claim 3, wherein selectively displaying the identification information comprises:

acquiring, from a second predefined position in the first document with respect to the first predefined label, contact information for one or more of the author and the publisher; and selectively displaying the contact information to the user.

5. The administrative interface of claim 1, wherein determining a level of authority to associate with the first analytic comprises:

assigning, by a publisher of the first analytic, a confidence score to the first analytic; and utilizing the confidence score, at least in part, to determine the level of authority to associate with the first analytic.

6. The administrative interface of claim 5, further comprising:

invalidating the confidence score associated with the first analytic based upon expiration of a predetermined amount of time.

7. The administrative interface of claim 1, wherein determining a level of authority to associate with the first analytic comprises:

receiving, from one or more users of the search method, user information indicating whether the one or more users determined the first analytic to be authoritative or helpful; and utilizing the user information, at least in part, to determine the level of authority to associate with the first analytic.

8. A system configured to be used with one or more databases for analytics comprising:

at least one processor; and a computer-readable medium configured to store instructions for execution by the at least one processor, wherein the instructions include:

specifying a first predefined label for use with the system;

receiving first input designating a first location of a first analytic;

obtaining a first document from the first location;

identifying the first predefined label within the first document;

obtaining a first datum associated with the first predefined label from the first document;

storing the first datum into a value index as a current value of the first analytic;

obtaining a second datum associated with the first predefined label from the first document;

storing the second datum into a text index as a textual description of the first analytic; and determining a level of authority to associate with the first analytic.

9. The system of claim 8, wherein determining a level of authority to associate with the first analytic comprises:

in response to obtaining the first document, acquiring, from a predefined position in the first document with respect to the first predefined label, identification information for one or more of an author and a publisher of the first analytic;

acquiring credibility data associated with the one or more of the author and the publisher of the first analytic;

determining a credibility value to associate with the first analytic based, at least in part, on the acquired credibility data; and utilizing the credibility value, at least in part, to determine the level of authority to associate with the first analytic.

10. The system of claim 9, further comprising:

selectively displaying the identification information for one or more of the author and a publisher of the first analytic to a user.

11. The system of claim 10, wherein selectively displaying the identification information comprises:

acquiring, from a second predefined position in the first document with respect to the first predefined label, contact information for one or more of the author and the publisher; and selectively displaying the contact information to the user.

12. The system of claim 8, wherein determining a level of authority to associate with the first analytic comprises:

assigning, by a publisher of the first analytic, a confidence score to the first analytic; and utilizing the confidence score, at least in part, to determine the level of authority to associate with the first analytic.

13. The system of claim 12, further comprising:

invalidating the confidence score associated with the first analytic based upon expiration of a predetermined amount of time.

14. The system of claim 8, wherein determining a level of authority to associate with the first analytic comprises:

receiving, from one or more users of the search method, user information indicating whether the one or more users determined the first analytic to be authoritative or helpful; and utilizing the user information, at least in part, to determine the level of authority to associate with the first analytic.

15. A non-transitory computer-readable medium storing processor-executable instructions, the instructions comprising:

specifying a first predefined label, wherein specifying the first predefined label includes using an administrative interface configured to be used with one or more databases for analytics;

receiving first input designating a first location of a first analytic;

obtaining a first document from the first location;

identifying the first predefined label within the first document;

obtaining a first datum associated with the first predefined label from the first document;

storing the first datum into a value index as a current value of the first analytic;

obtaining a second datum associated with the first predefined label from the first document;

storing the second datum into a text index as a textual description of the first analytic; and determining a level of authority to associate with the first analytic.

16. The non-transitory computer-readable medium storing processor-executable instructions of claim 15, wherein determining a level of authority to associate with the first analytic comprises:

in response to obtaining the first document, acquiring, from a predefined position in the first document with respect to the first predefined label, identification information for one or more of an author and a publisher of the first analytic;

acquiring credibility data associated with the one or more of the author and the publisher of the first analytic;

determining a credibility value to associate with the first analytic based, at least in part, on the acquired credibility data; and utilizing the credibility value, at least in part, to determine the level of authority to associate with the first analytic.

17. The non-transitory computer-readable medium storing processor-executable instructions of claim 16, further comprising:

selectively displaying the identification information for one or more of the author and a publisher of the first analytic to a user;

acquiring, from a second predefined position in the first document with respect to the first predefined label, contact information for one or more of the author and the publisher; and selectively displaying the contact information to the user.

18. The non-transitory computer-readable medium storing processor-executable instructions of claim 15, wherein determining a level of authority to associate with the first analytic comprises:

assigning, by a publisher of the first analytic, a confidence score to the first analytic; and utilizing the confidence score, at least in part, to determine the level of authority to associate with the first analytic.

19. The non-transitory computer-readable medium storing processor-executable instructions of claim 18, further comprising:

invalidating the confidence score associated with the first analytic based upon expiration of a predetermined amount of time.

20. The non-transitory computer-readable medium storing processor-executable instructions of claim 15, wherein determining a level of authority to associate with the first analytic comprises:

receiving, from one or more users of the search method, user information indicating whether the one or more users determined the first analytic to be authoritative or helpful; and utilizing the user information, at least in part, to determine the level of authority to associate with the first analytic.

* * * * *